United States Patent
Luo et al.

(10) Patent No.: US 10,550,080 B2
(45) Date of Patent: Feb. 4, 2020

(54) ACYL SULFONAMIDE NAV1.7 INHIBITORS

(71) Applicant: BRISTOL-MYERS SQUIBB COMPANY, Princeton, NJ (US)

(72) Inventors: Guanglin Luo, Newtown, PA (US); Ling Chen, Doylestown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/092,075

(22) PCT Filed: Apr. 19, 2017

(86) PCT No.: PCT/US2017/028217
§ 371 (c)(1),
(2) Date: Oct. 8, 2018

(87) PCT Pub. No.: WO2017/184658
PCT Pub. Date: Oct. 26, 2017

(65) Prior Publication Data
US 2019/0119209 A1    Apr. 25, 2019

Related U.S. Application Data

(60) Provisional application No. 62/325,375, filed on Apr. 20, 2016.

(51) Int. Cl.
| | | |
|---|---|---|
| A61K 31/404 | (2006.01) |
| A61K 31/416 | (2006.01) |
| C07D 209/32 | (2006.01) |
| C07D 231/56 | (2006.01) |
| C07D 401/04 | (2006.01) |
| C07D 401/14 | (2006.01) |
| C07D 403/04 | (2006.01) |
| C07D 409/12 | (2006.01) |
| A61P 25/04 | (2006.01) |

(52) U.S. Cl.
CPC ........ *C07D 209/32* (2013.01); *C07D 401/04* (2013.01); *C07D 401/14* (2013.01); *C07D 403/04* (2013.01); *C07D 409/12* (2013.01); *A61P 25/04* (2018.01)

(58) Field of Classification Search
CPC .. A61K 31/404; A61K 31/416; C07D 209/32; C07D 231/56; C07D 401/04; C07D 401/14; C07D 403/04; C07D 409/12; A61P 25/04
USPC ........ 514/415, 414, 406; 548/511, 510, 503, 548/361.1, 362.5
See application file for complete search history.

(56) References Cited

FOREIGN PATENT DOCUMENTS

WO    WO 2012/085781 A1    6/2012

*Primary Examiner* — Matthew P Coughlin
*Assistant Examiner* — Sagar Patel
(74) *Attorney, Agent, or Firm* — Elliott Korsen

(57) ABSTRACT

The present disclosure relates to compounds of formula I which inhibit NaV1.7, and include pharmaceutically acceptable salts, compositions comprising such compounds, and methods using and making such compounds and compositions.

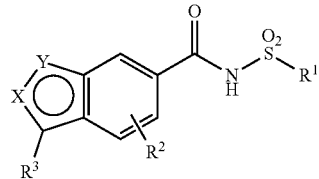

9 Claims, No Drawings

ACYL SULFONAMIDE NAV1.7 INHIBITORS

CROSS REFERENCE TO RELATED APPLICATION

This application claims priority to U.S. Provisional Patent Application Ser. No. 62/325,375, filed Apr. 20, 2016, which is incorporated by reference in its entirety.

BACKGROUND OF THE INVENTION

Voltage-gated sodium (NaV) channels are responsible for the upstroke of the action potential in most excitable cells, including nerve cells [Hille, B. Ion channels of excitable membranes. (2001), $3^{rd}$ ed, Sinauer Associates, Sunderland, Mass.]. NaV channels open in response to membrane depolarization and generate an inward current that underlies the upstroke of the action potential. In general, NaV channels open quickly (within msec) in response to depolarization and then just as rapidly close by a process called inactivation. Thus, these channels can exist in several different conformations or 'states' whose occupancy is governed by membrane voltage.

NaV channels are composed of a pore-forming alpha subunit responsible for ion conduction and gating [Catterall, W A, J. Physiol. 590(11): 2577-2599, (2012)]. These large single polypeptides (>250 kDa) are organized into four functional domains (DI-DIV), each with 6 transmembrane segments (S1-S6). Each domain can be further subdivided into the voltage-sensor domain (VSD) comprised of segments S1-S4 and the pore domain comprised of segments S5-S6. In addition to the alpha subunit, NaV channels have associated beta subunits which have a single transmembrane segment and a large extracellular immunoglobin-like region. Beta subunits modulate expression, gating and localization of the alpha subunit and interact with the extracellular matrix and intracellular cytoskeleton [Isom, L L, Neuroscientist, 7(1):42-54, (2001)].

Nine mammalian NaV alpha subunit genes exist. Based on the established nomenclature, they are referred to as NaV1.1-NaV1.9 [Goldin, A L et al., Neuron 28(2): 365-368, (2000)]. In addition to the primary sequences and homology, individual NaV1 family members are characterized by specific gating properties, localization and pharmacology [Catterall, W A, Goldin A L and SG Waxman, Pharmacol. Rev. 57(4):397-409, (2005)]. For example, NaV1.5 is expressed almost exclusively in the heart and is weakly sensitive to the neurotoxin tetrodotoxin (TTX). In contrast, NaV1.7 is mostly expressed in peripheral sensory neurons and is TTX-sensitive. A second sub-family of NaVs channels (NaV2/NaG) also exists [Wantanabe, E et al., J. Neurosci., 20(20):7743-7751, (2000)].

Several sites of drug action on NaV channels are known, based primarily on mutagenesis studies. For example, local anesthetic molecule binding has been mapped to specific residues on the S6 segment of DI, DIII and DIV [Ragsdale, D S et al. Science 265(5179):1724-1728, (1994); Ragsdale D S et al., Proc. Natl. Acad. Sci. USA 93(17):9270-9275; Yarov-Yarovoy, V et al., J. Biol. Chem. 276(1):20-27, (2001); Yarov-Yarovoy, V et al., J. Biol. Chem. 277(38): 35393-35401, (2002)]. Six neurotoxin receptor sites (Sites 1-6) on NaV channels have been identified (reviewed in [Catterall, W A et al., Toxicon 49(2):124-141, (2007)]). Site 1 binds the pore-blockers tetrodotoxin and saxitoxin and is formed by residues of the pore loops of all four domains [Noda, M et al., FEBS Lett. 259(1):213-216, (1989); Terlau, H et al., FEBS Lett. 293(1-2):93-96, (1991)]. Site 2 binds lipid soluble toxins like veratridine and batrachotoxin and maps to S6 residues in D1 and DIV [Trainer, V L et al., J. Biol. Chem. 271(19):11261-11267, (1996); Kimura, T et al. FEBS Lett. 465:18-22, (2000)]. Alpha scorpion toxins bind to Site 3 which includes the S3-S4 loop of DIV [Rogers, J C et al., J. Biol. Chem. 271: 15950-15962, (1996)]. Site 4 binds beta scorpion toxins and includes the S3-S4 loop of DII [Cestele, S et al., J. Biol. Chem. 282:21332-21344, (1998)]. Site 5 is where the so-called red-tide toxins like brevetoxin bind and includes the S6 of D1 and S5 of DIV [Trainer, V L et al., Mol. Pharmacol. 40(6):988-994, (1991); Trainer, V L et al., J. Biol. Chem. 269(31):19904-19909, (1994)]. Delta-conotoxins bind to Site 6 which includes residues in S4 of DIV [Leipold, E, et al., FEBS Lett 579(18):3881-3884, (2005)].

Significant genetic data points to a role of NaV1.7 (SCN9A) in human pain perception. Most dramatically, rare mutations in SCN9A which result in loss-of-function of NaV1.7 protein cause congenital insensitivity to pain (CIP) in humans [Cox, J J et al., Nature 444(7121): 894-898, (2006); Goldberg, Y P et al., Clin. Genet. 71(4):311-319, (2007); Ahmad, S et al., Hum. Mol. Genet. 16(17): 2114-2121, (2007)]. These patients have normal intelligence but are unable to sense pain, even to stimuli which case significant injury. The only other significant deficit in these patients is anosmia, presumably due to a role of NaV1.7 in olfaction. Studies in genetically modified mice also point to a key role of NaV1.7 in pain perception. Deletion of Nav1.7 in both sensory and sympathetic neurons of mice abolishes mechanical, inflammatory and neuropathic pain responses [Minett, M S et al., Nat. Commun. 3:791, (2012)]. Recently, global gene disruption of SCN9A in mice has been reported to recapitulate the CIP phenotype [Gingras, J et al. PLoS One 9(9): e105895, (2014)]. Furthermore, inducible deletion of NaV1.7 in DRGs of adult mice reverses neuropathic pain [Minett, M S et al., Cell Rep. 6(2): 301-312, (2014)], suggesting that pharmacological inhibition of NaV1.7 channels in humans will be analgesic. In addition to the compelling evidence from these loss-of-function studies, spontaneous inherited pain syndromes in humans have been linked to gain-of-function of NaV1.7. Specifically, three syndromes in humans are linked to mutations in SCN9A: inherited erythromelalgia (IEM) [Yang, Y et al., J. Med. Genet. 41(3): 171-174, (2004)], paroxysmal extreme pain disorder (PEPD) [Fertleman, C R et al., Neuron 52(5):767-774, (2006)] and small fiber neuropathy (SFN) [Faber, C G et al. Ann. Neurol. 71(1): 26-39, (2012)]. In general, mutations in SCN9A linked to IEM result in enhanced channel activation where PEPD mutations result in impaired fast inactivation (reviewed in [Dib-Hajj, S D et al., Nat. Rev. Neurosci. 14(1): 49-62, (2013)]). Mutations linked to SFN alter fast inactivation and/or slow inactivation [Faber, C G et al. Ann. Neurol. 71(1): 26-39, (2012)].

Given the importance of NaV1.7 in pain perception, considerable effort has been expended to identify selective inhibitors of the channel. Peptides identified from venom are common sources of potent ion channel modifiers. For NaV1.7, the peptide ProTx-II from tarantula was first identified as an inhibitor of NaV1.8 [Middleton, R E et al. Biochemistry 41(50): 14734-14747, (2002)] and later found to be approximately 100-fold selective for NaV1.7 over other NaV channels [Schmalhofer, W A et al. Mol. Pharmacol. 74(5): 1476-1484, (2008)]. ProTx-II binding determinants are primarily in the VSD of DII and DIV whereas the related peptide, Huwentoxin-IV, is thought to interact primarily with the DII VSD [Xiao, Y et al., Mol. Pharmacol. 78(6): 1124-1134, (2010)]. Extensive structure-activity studies of ProTx-II have yielded peptides with potencies in the picomolar range [Park, JH et al. J. Med. Chem. 57(15): 6623-6631, (2014)]. Structure-based engineering of another tarantula peptide, GpTx-1, has yielded peptides with optimized potency and selectivity [Murry, JK et al., J. Med. Chem. 58(5): 2299-2314, (2015)].

Efforts to identify small molecular weight inhibitors of NaV1.7 have been extensive. Numerous NaV1.7 blockers have been reported in the literature (reviewed in [de Lera Ruiz, M and RL Kraus, J. Med. Chem. 58(18) 7093-7118, (2015)]) although most do not have sufficient selectivity over other NaV subtypes. A significant advance came with the discovery of a class of arylsulfonamides with subtype selectivity [McCormack, K et al., Proc. Natl. Acad. Sci. USA, 110(29): E2724-E2732, (2013)]. Some members of the series include molecules that are highly selectivity for NaV1.7. Three residues in the VSD of DIV were identified as conferring potent inhibition by one such molecule, PF-04856264. The recent co-crystal structure of a chimeric channel consisting of a portion of the NaV1.7 DIV VSD grafted onto the bacterial NaV channel NavAb with a related arylsulfonamide bound defines some of the primary interactions between this class of molecules and the NaV1.7 DIV VSD [Ahuja S, et al., Science 350(6267): aac5464, (2015)]. These studies point to the possibility of discovering highly potent and selective inhibitors of NaV1.7 with properties suitable for use as oral analgesics.

DESCRIPTION OF THE INVENTION

The present disclosure relates to compounds of formula I, which inhibit NaV1.7, and include pharmaceutically acceptable salts, compositions comprising such compounds, and methods using and making such compounds and compositions.

One aspect of the invention is a compound of formula I

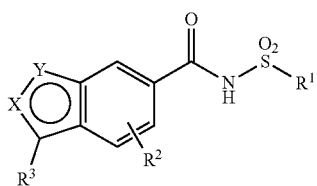

where:
X is CH and Y is $NR^4$;
or X is $NR^5$ and Y is N;
or X is N and Y is $NR^5$;
$R^1$ is alkyl, haloalkyl, cycloalkyl, $NR^6R^7$, or $Ar^1$;
$R^2$ is hydrogen or halo;
$R^3$ is phenyl, pyridinyl, pyridazinyl, pyrimidinyl, or pyrazinyl, and is substituted with 0-3 substituents selected from cyano, halo, alkyl, haloalkyl, alkoxy, (cycloalkyl)alkoxy, haloalkoxy, and $NHCO_2R^8$;
$R^4$ is hydrogen or alkyl;
$R^5$ is hydrogen or alkyl;
$R^6$ is hydrogen or alkyl;
$R^7$ is hydrogen or alkyl;
or $NR^6R^7$ taken together is azetidinyl, pyrrolidinyl, piperidinyl, piperazinyl, or morpholinyl, and is substituted with 0-3 halo or alkyl substituents;
$R^8$ is alkyl; and $Ar^1$ is phenyl or thienyl and is substituted with 0-3 substituents selected from cyano, halo, alkyl, haloalkyl, alkoxy, and haloalkoxy;
or a pharmaceutically acceptable salt thereof.

Another aspect of the invention is a compound of formula I where X is CH and Y is $NR^4$.

Another aspect of the invention is a compound of formula I where X is $NR^5$ and Y is N.

Another aspect of the invention is a compound of formula I where X is N and Y is $NR^5$.

Another aspect of the invention is a compound of formula I where $R^3$ is phenyl substituted with 0-3 substituents selected from cyano, halo, alkyl, haloalkyl, alkoxy, (cycloalkyl)alkoxy, haloalkoxy, and $NHCO_2R^8$.

Another aspect of the invention is a compound of formula I where $R^3$ is pyridinyl, pyridazinyl, pyrimidinyl, or pyrazinyl, and is substituted with 0-3 substituents selected from cyano, halo, alkyl, haloalkyl, alkoxy, (cycloalkyl)alkoxy, haloalkoxy, and $NHCO_2R^8$.

Another aspect of the invention is a compound of formula I where $Ar^1$ is phenyl substituted with 0-3 substituents selected from cyano, halo, alkyl, haloalkyl, alkoxy, and haloalkoxy.

For a compound of Formula I, the scope of any instance of a variable substituent, including X, Y, $R^1$, $R^2$, $R^3$, $R^4$, $R^5$, $R^6$, $R^7$, $R^8$, and $Ar^1$, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. Terms with a hydrocarbon moiety (e.g. alkoxy) include straight and branched isomers for the hydrocarbon portion which are composed of 1 to 6 carbons. "Halo" includes fluoro, chloro, bromo, and iodo. "Haloalkyl" and "haloalkoxy" include all halogenated isomers from monohalo to perhalo "Aryl" means a monocyclic or bicyclic aromatic ring system having 5 to 12 carbon atoms wherein one or both of the rings are aromatic. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Automated Electrophysiology: Ion Works Barracuda population patch clamp (PPC). PPC measurements were performed using an IonWorks Barracuda instrument (Molecular Devices Corporation, Union City, Calif.) using either PatchPlate™ PPC substrates (Molecular Devices Corporation) with 64 apertures per well. The ability to average currents from 64 recordings from each well greatly improves data consistency and recording success rates in the measurement of NaV1.7 mediated ionic currents. Calculated leak current was digitally subtracted from the total cell NaV1.7 current for each sample point acquired.

NaV1.7 currents were elicited by a voltage clamp protocol designed to bias the NaV1.7 channels to their inactivated state as follows. From holding potential of −60 mV cells were briefly hyperpolarized to −100 mV for 1.25 sec, then stepped to −20 mV for 20 sec to inactivate the channels. This was followed by a relatively brief hyperpolarization to −100 mv for 300 ms, then a 20 msec test pulse to −20 mV to elicit the NaV1.7 current used to measure the pharmacology of all test compounds. Compounds were incubated for 600 sec between the pre- and post-compound reads. The external recording solution used was (in mM) 137 NaCl, 4 KCl, 1 MgCl$_2$, 1.8 CaCl$_2$, 10 Hepes, 10 glucose, pH to 7.4 with NaOH, and the internal solution used was (in mM) 100 K-gluconate, 40 KCl, 3.2 zMgCl$_2$, 5 EGTA, 10 HEPES pH to 7.2 with KOH. The same solutions were used to record NaV1.5 currents, with the following voltage clamp protocol. NaV1.5 currents were elicited by a voltage clamp protocol designed to bias the NaV1.5 channels to their inactivated state as follows. From holding potential of −40 mV cells were briefly hyperpolarized to −100 mV for 300 ms, then stepped to −10 mV for 20 sec to inactivate the channels. This was followed by a relatively brief hyperpolarization to −100 mv for 30 ms, then a 20 msec test pulse to −10 mV to elicit the NaV1.5 current used to measure the pharmacology of all test compounds.

HEK 293 cells expressing NaV1.7 and NaV1.5 channels, were used (Essen Biosciences, Ann Arbor, Mich.). Cells were cultured in T-175 flasks and passaged every 2 to 3 days at 1:3 to 1:6 seeding density dilutions. Cells were grown to 70% to 90% confluence in a flask and removed from the incubator (37° C., 5% CO2) 1 to 3 days after plating. Growth medium was aspirated from the culture flasks. Cells were gently rinsed with 10 ml of PBS (Catalog number: 14190144, Gibco) to remove residual media. Next a total of 2 mL TrypLE (Gibco) solution was added, and the flasks containing cells were sat for 3 min at RT, after which, the cells became visibly rounded and were easily dislodged from the bottom of the flask with a few brief taps on a solid surface. A total of 8 mL of media was added to the flask to inactivate the TrypLE, and the mixture was centrifuged at 910 rpm for 4 min. The cell supernatant was decanted, and the cell pellets were resuspended in 5-6 mL of external solution followed by gentle triturations using a 10 ml pipette, and transferred to a 15 ml conical tube and immediately brought to the IW Barracuda instrument. The cell suspension had a final concentration of ~2 to 3 million cells per ml; this corresponds to 10,000 cells added per well.

Peak membrane currents were analyzed with IW Barracuda software and exported to Excel for further analysis. Concentration response curve fitting was performed with BMS in-house software. IC$_{50}$ values were obtained by fits of the Hill equation to the average percent inhibition data plotted versus compound concentration. Concentration-response curves for all test compounds were fitted to a 4-parameter equation: % of control=100 (1+([drug]/IC50) p)−1, where IC50 is the concentration of drug required to inhibit current by 50% and p is the Hill slope. Results are reported in Table 1 (NaV1.7 Barra IC$_{50}$ in nM and NaV1.5 Barra IC$_{50}$ in nM).

Ligand Binding Assay (LBA): hNaV1.7 binding affinities were determined with a filtration binding assay using purified membranes from HEK293 cells stably expressing hNaV1.7. HEK293 cells from a 10-stack cell culture flask (approximately 10$^{10}$ cells) were dissociated, frozen, and stored at −80° C. To prepare membranes, the frozen cell pellet was thawed and suspended in 6 ml hypotonic lysis buffer (50 mM HEPES, 0.1% mammalian protease inhibitor cocktail). 1 ml of resuspended cells was added to an additional 6 ml of lysis buffer and homogenized with 30 strokes of a tight pestle in a glass homogenizer. Homogenate was centrifuged at 1000×g for 10 minutes at 4° C. and the resulting supernatant was further centrifuged at 38,500×g for 60 minutes at 4° C. The resulting pellet was resuspended in binding buffer (50 mM HEPES, 130 mM NaCl, 5.4 mM KCl, 0.8 mM MgCl$_2$, 5 mM glucose, pH 7.4) and needle homogenized with a 25 gauge needle. Protein concentration was determined with a BCA protein assay. Purified membranes were aliquoted, flash frozen in an ethyl alcohol dry ice bath, and stored at −80° C. To measure displacement of a radiolabeled ligand, 50 µg of purified hNaV1.7 HEK cell membranes were incubated with test compounds (eight concentrations, in duplicate) and 0.5 nM [3H] labeled radioligand in a 96 well plate for 24 hours at room temperature on a shaker. The total binding reaction volume was 250 µl, consisting of 200 µl purified hNaV1.7 HEK cell membranes, 25 µl test compound, and 25 µl radioligand. Non-specific binding was defined by 20 µM of a reference hNaV1.7 inhibitor. Binding reactions were terminated by filtration through GF/B filters presoaked in 0.5% polyethyleneamine.

Filters were washed 5 times with 2 ml each of 4'C wash buffer (50 mM Tris-HCl, pH 7.4 at 4° C.). Bound radioactivity captured on the filters was counted on a liquid scintillation counter. Specific binding, expressed as % inhibition, was fit with Graphpad Prism software to determine binding $IC_{50}$ values. Results are reported in Table 1 (NaV1.7 LBA $IC_{50}$ in nM).

TABLE 1

| Example | NaV1.7 Barra $IC_{50}$ nM | NaV1.7 LBA $IC_{50}$ nM | NaV1.5 Barra $IC_{50}$ nM |
| --- | --- | --- | --- |
| 1 | 85 | 422 | 19,626 |
| 2 | 90 | 91 | 18,347 |
| 3 | 2860 | 4940 | >30,000 |
| 4 | 80 | 243 | 18,282 |
| 5 | 743 | 7270 | >30,000 |
| 6 | >30,000 | >30000 | >30,000 |
| 7 | >30,000 | | >30,000 |
| 8 | >30,000 | | |
| 9 | >30,000 | >20000 | >30,000 |
| 10 | 739 | 1030 | >30,000 |
| 11 | 604 | 750 | 8,638 |
| 12 | 363 | 317 | >30,000 |
| 13 | 1420 | 290 | >30,000 |
| 14 | 173 | 554 | >30,000 |
| 15 | 375 | 943 | >30,000 |
| 16 | 427 | 217 | >30,000 |
| 17 | 220 | 440 | >30,000 |
| 18 | 109 | 77 | 8,718 |
| 19 | 812 | 1080 | 7,477 |
| 20 | 419 | 361 | 3,859 |
| 21 | >30,000 | >30000 | 18,123 |
| 22 | 525 | 275 | |
| 23 | 183 | 468 | >30,000 |
| 24 | 294 | 22 | 11,989 |
| 25 | 1,280 | | 6,331 |
| 26 | 4,176 | | 8,766 |
| 27 | 3,330 | | 23,658 |
| 28 | 8,050 | | 11,287 |
| 29 | 703 | 89 | 1,487 |
| 30 | 262 | 1010 | >30,000 |
| 31 | 69 | 321 | >30,000 |
| 32 | 1,906 | | >30,000 |
| 33 | 1,920 | | 24,494 |
| 34 | 189 | 270 | 8,368 |
| 35 | 86 | 52 | 15,105 |
| 36 | 154 | 38 | 5,673 |
| 37 | 458 | 207 | 14,012 |
| 38 | 1300 | 156 | 21,890 |
| 39 | 66 | 67 | 6,508 |
| 40 | 787 | 1,993 | 16,729 |
| 41 | 195 | 673 | 11,303 |
| 42 | 524 | 11 | 7,175 |
| 43 | 310 | 3.4 | 4,852 |
| 44 | 104 | 86 | 18,711 |
| 45 | 59 | 26 | 3,697 |
| 46 | 49 | 84 | >30,000 |
| 47 | 16 | 39 | 3,818 |
| 48 | 91 | 956 | >30,000 |
| 49 | 38 | 146 | 9,666 |

Pharmaceutical Composition and Methods of Use

The compounds of this invention inhibit NaV1.7. Accordingly, another aspect of the invention is a pharmaceutical composition comprising a therapeutically effective amount of a compound of Formula I, or a pharmaceutically acceptable salt thereof, and a pharmaceutically acceptable carrier.

Another aspect of the invention is a method for treating pain in a patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of pain.

"Therapeutically effective" means the amount of agent required to provide a meaningful patient benefit as understood by practitioners in the field of pain.

"Patient" means a person afflicted with pain and suitable for therapy as understood by practitioners in the field.

"Treatment," "therapy," "regimen," and related terms are used as understood by practitioners in the field.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

Chemical Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the claims, rather than to the foregoing examples, and all changes which come within the meaning and range of equivalency of the claims are therefore intended to be embraced.

Compounds of formula 6 can be prepared by the methods outlined in Scheme I. Treatment of indole 1 with NBS can afford indole 2. Alkylation of the amino group in 2 with an alkyl halide in the presence of a base such as potassium carbonate or sodium hydride in an appropriate solvent such as DMF or DCM can give compounds of formula 3. The ester in compounds of formula 3, can be hydrolyzed with as LiOH in solvents such as THF, MeOH, water, and combinations thereof to afford compounds of formula 4. Sulfonamide formation can be effected by treatment of the acid with a reagent such as 2-chloro-1-methylpyridin-1-ium iodide in a solvent such as DCM in the presence of DMAP followed by addition of an alkylsulfonamide in the presence of a base such as TEA to form compounds of formula 5. The bromide can optionally be replaced with other substituents by using a palladium catalyzed coupling reaction, such as a Suzuki reaction, using conditions known in the art. This can include reaction of 5 with an aryl, heteroaryl, alkenyl boronic acid in the presence of a base such as sodium carbonate and a catalyst such as PdCl2(dppf) or Pd$_2$(dba)$_3$ in a solvent such as toluene or 1,4-dioxane at temperatures ranging from 20° C. to 150° C. to give compounds of the formula 6.

General Scheme I:

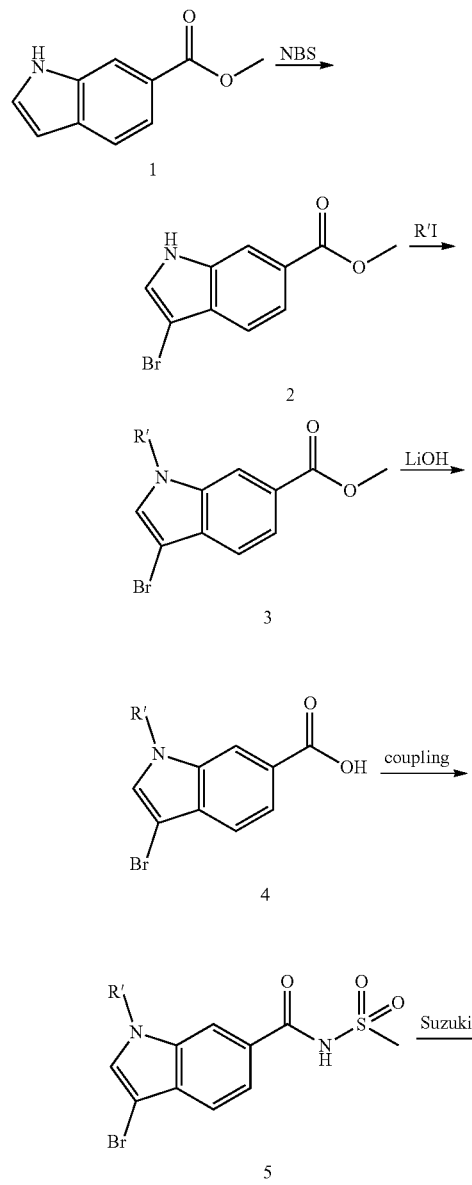

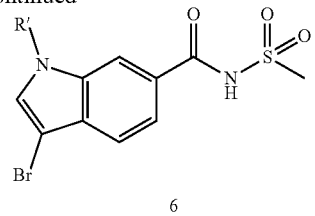

Compounds of formula 11 can be prepared by the methods outlined in Scheme II. Halogenation of indole 1 with a reagent such as NIS, NBS, NCS, or I2 can afford indole 7. Alkylation of the indole with an alkyl halide in the presence of a base such as potassium carbonate or sodium hydride in an appropriate solvent such as DMF or DCM can give compounds of formula 8. The bromide can optionally be replaced with other substituents by using a palladium catalyzed coupling reaction, such as a Suzuki reaction, using conditions known in the art. This can include reaction of 8 with an aryl, heteroaryl, alkenyl boronic acid in the presence of a base such as sodium carbonate and a catalyst such as PdCl2(dppf) or Pd$_2$(dba)$_3$ in a solvent such as toluene or 1,4-dioxane at temperatures ranging from 20° C. to 150° C. to give compounds of the formula 9. The ester in compounds of formula 9, can be hydrolyzed with as LiOH in solvents such as THF, MeOH, water, and combinations thereof to afford compounds of formula 10. Sulfonamide formation can be effected by treatment of the acid with a reagent such as 2-chloro-1-methylpyridin-1-ium iodide in a solvent such as DCM in the presence of DMAP followed by addition of an alkylsulfonamide in the presence of a base such as TEA to form compounds of formula 11.

General Scheme II:

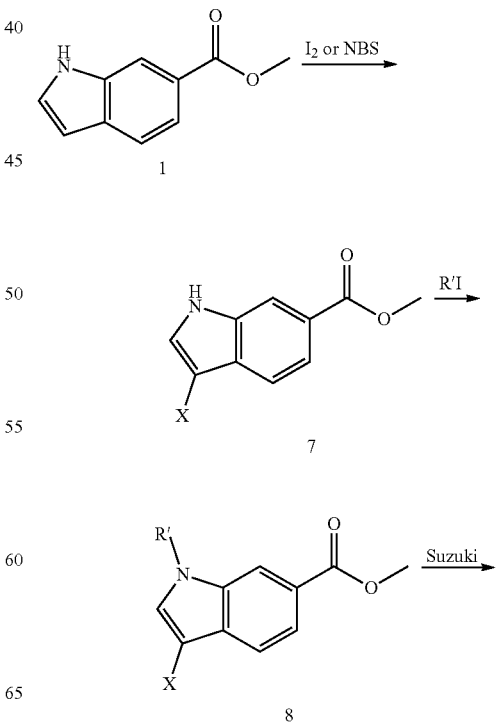

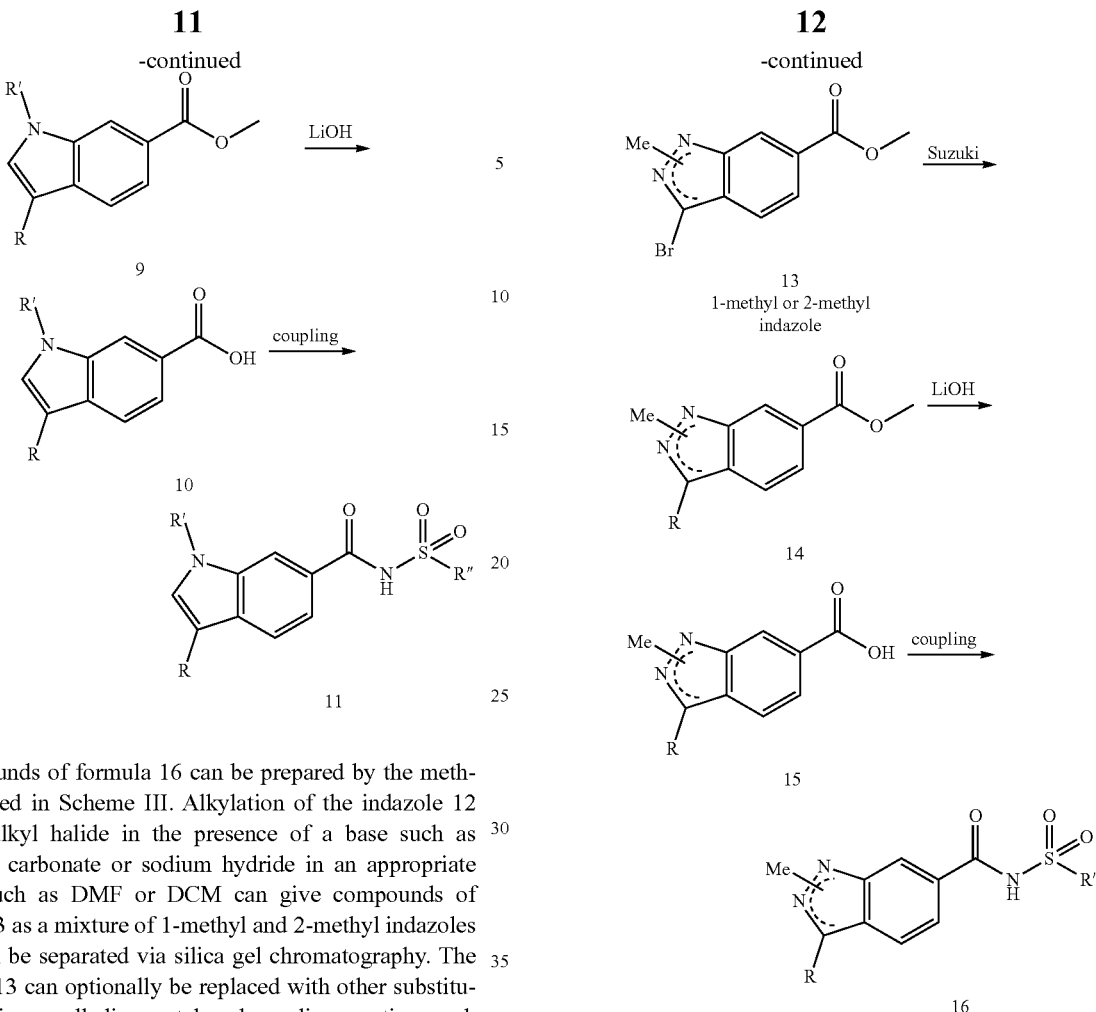

Compounds of formula 16 can be prepared by the methods outlined in Scheme III. Alkylation of the indazole 12 with an alkyl halide in the presence of a base such as potassium carbonate or sodium hydride in an appropriate solvent such as DMF or DCM can give compounds of formula 13 as a mixture of 1-methyl and 2-methyl indazoles which can be separated via silica gel chromatography. The halide of 13 can optionally be replaced with other substituents by using a palladium catalyzed coupling reaction, such as a Suzuki reaction, using conditions known in the art. This can include reaction of 13 with an aryl, heteroaryl, alkenyl boronic acid in the presence of a base such as sodium carbonate and a catalyst such as PdCl2(dppf) or $Pd_2(dba)_3$ in a solvent such as toluene or 1,4-dioxane at temperatures ranging from 20° C. to 150° C. to give compounds of the formula 14. The ester in compounds of formula 14, can be hydrolyzed with as LiOH in solvents such as THF, MeOH, water, and combinations thereof to afford compounds of formula 15. Sulfonamide formation can be effected by treatment of the acid with a reagent such as 2-chloro-1-methylpyridin-1-ium iodide in a solvent such as DCM in the presence of DMAP followed by addition of an alkylsulfonamide in the presence of a base such as TEA to form compounds of formula 16.

General Scheme III:

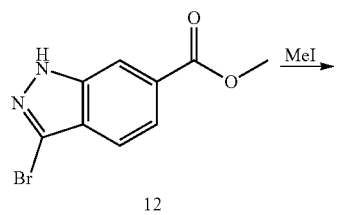

Compounds of formula 24 can be prepared by the methods outlined in Scheme IV. Compound 17 can be nitrated by heating in the present of a mixture of nitric and sulfuric acid to give compounds of formula 18. Esterification with MeOH and sulfuric acid can afford compounds of the formula 19. Condensation with N,N-dimethylmethanamine in a solvent such as DMF affords compounds of formula 20. Reduction of the nitro group with PD/C in the presence of hydrogen effects cyclization can form compounds of the formula 21. Halogenation of indole 21 with a reagent such as 12 in the presence of KOH can afford indole 22. The ester can be hydrolyzed with as LiOH in solvents such as THF, MeOH, water, and combinations thereof to afford compounds of formula 23. Compounds of the formula 24 can be then prepared from compounds of the formula 23 utilizing the methods described in Scheme II.

General Scheme IV:

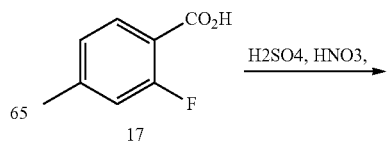

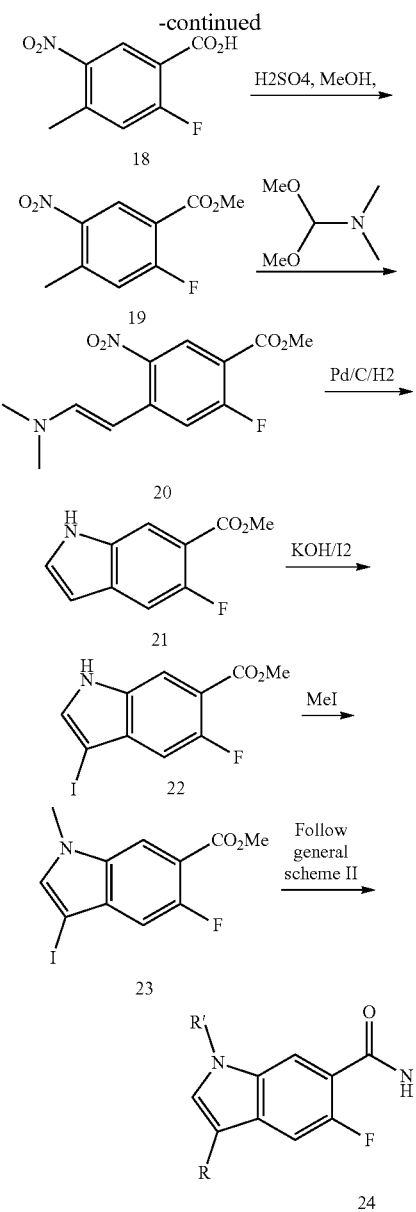

Water: 10 mM Ammonium Acetate; Solvent B=95% MeOH: 5% Water: 10 mM Ammonium Acetate; Flow rate: 1 mL/min; Starting B=0%; Final B=100%; Gradient time=2 min; Run time: 3 min.

LC/MS Method B:
Column: Phenomenex LUNA C18, 30×2, 3 m; Solvent A=10% MeOH: 90% Water: 0.1% TFA; Solvent B=90% MeOH: 10% Water: 0.1% TFA; Flow rate: 1 mL/min; Starting B=0%; Final B=100%; Gradient time=2 min; Run time: 3 min.

LC/MS Method C:
Column: Phenomenex LUNA C18, 30×2, 3 m; Solvent A=5% MeOH: 95% Water: 10 mM Ammonium Acetate; Solvent B=95% MeOH: 5% Water: 10 mM Ammonium Acetate; Flow rate: 0.8 mL/min; Starting B=0%; Final B=100%; Gradient time=4 min; Run time: 5 min.

LC/MS Method D:
Column: Waters Acquity UPLC BECH C18, 2.1×50 mm, 1.7 um particles; Solvent A=5% MeCN: 95% Water: 0.1% Trifluoroacetic Acid; Solvent B=95% MeCN: 5% Water: 0.1% Trifluoroacetic Acid; Flow rate: 1.0 mL/min; Starting B=0%; Final B=100%; Gradient time=3 min; Run time: 3.75 min. Temperature: 50° C.; UV at 220 nm

INTERMEDIATE A

Methyl 3-bromo-1H-indole-6-carboxylate

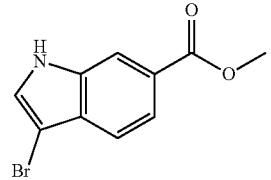

To a DMF (60 mL) solution of methyl 1H-indole-6-carboxylate (5.1 g, 29.1 mmol) at −60° C. was added a DMF solution (40 mL) of NBS (5.70 g, 32.0 mmol) dropwise. The reaction mixture was stirred for 2 hours while it was warmed up to room temperature. The reaction mixture was then poured into ice water (1 L) and the precipitate formed was collected through via vacuum filtration. The solid was washed with water. The solid was dissolved in ethyl acetate and washed twice with sat. aq. NaCl. The ethyl acetate layer was separated, dried (Na2SO4), filtered and concentrated to give the crude product. The material was carried on without further purification. LCMS (ESI) m/e 254.1 [(M+H)$^+$, calcd $C_{10}H_9Br_1N_1O_2$, 253.9]; LC/MS retention time (method A): $t_R$=1.63 min.

INTERMEDIATE B

Methyl 3-iodo-1H-indole-6-carboxylate

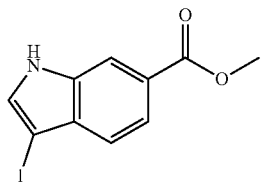

The abbreviations used in the present application, including in the illustrative schemes and examples which follow, are known in the art. Some of the abbreviations used are as follows: THF for tetrahydrofuran; MeOH for methanol; DMF for N,N-dimethylformamide; DCM for dichloromethane; Me for methyl; Ph for phenyl; EtOH for ethanol; TEA or Et$_3$N for triethylamine; Ac for acetyl; dppf for 1,1'-bis(diphenylphosphanyl) ferrocene; DMAP for N,N-dimethylaminopyridine; RT or rt or r.t. for room temperature or retention time (context will dictate); $t_R$ for retention time; NBS for N-bromosuccinimide; min for minutes; h for hours; MeCN or ACN for acetonitrile; EtOAc for ethyl acetate; DIAD for diisopropyl azodicarboxylate; DMSO for dimethylsulfoxide; LCMS or LC/MS for liquid chromatography-mass spectrometry, NMR for nuclear magnetic resonance, TLC for thin layer chromatography, UV for ultraviolet.

Analytical LC/MS Methods:
LC/MS Method A:
Column: Phenomenex LUNA C18, 30×2, 3 m; Solvent A=5% MeOH: 95%

A mixture of KOH (1.79 g, 31.9 mmol) and methyl 1H-indole-6-carboxylate (2.31 g, 13.17 mmol) in DMF (30 mL) was stirred at room temperature for 1 hour. Iodine (3.34 g, 13.17 mmol) in DMF (7 mL) was added to the reaction mixture at room temperature. The stirring was continued for 18 hours, the mixture was poured into 400 mL ice water. The solid that formed was collected by vacuum filtration and washed with water. The solid was dissolved in ethyl acetate and dried with $Na_2SO_4$. The ethyl acetate layer was filtered and concentrated to give the crude product as a brown solid. The material was stored in the refrigerator and used as needed. $^1$H NMR (400 MHz, CHLOROFORM-d) δ 8.67-8.53 (s, 1H), 8.15 (d, J=0.8 Hz, 1H), 7.90 (dd, J=8.4, 1.4 Hz, 1H), 7.50 (d, J=8.5 Hz, 1H), 7.46 (d, J=2.8 Hz, 1H), 3.96 (s, 3H); LCMS (ESI) m/e 300.0 [(M–H)+, calcd $C_{10}H_7I_1N_{10}O_2$, 300.0]; LC/MS retention time (method B): $t_R$=1.71 min.

INTERMEDIATE C

Methyl 3-bromo-1-methyl-1H-indole-6-carboxylate

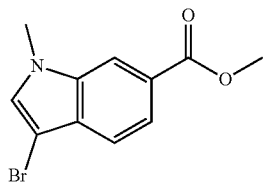

Potassium carbonate (1.681 g, 12.16 mmol) was added to a solution of methyl 3-bromo-1H-indole-6-carboxylate (1.0299 g, 4.05 mmol) in DMF (10 mL) at room temperature. The mixture was stirred at room temperature for 30 min. The reaction mixture was cooled to 0° C. and methyl iodide (0.304 mL, 4.86 mmol) was added. The reaction was stirred overnight while it warmed up to room temperature. The reaction was diluted with water and extracted with diethyl ether three times. The diethyl ether layers were combined, dried (Na2SO4), filtered, and concentrated under reduced pressure. The residue was purified via silica gel flash column chromatography eluting with ethyl acetate in hexane from 0 to 25% to afforded the title compound as a white solid (0.978 g, 90% yield). $^1$H NMR (400 MHz, CHLOROFORM-d) δ 8.12-8.09 (m, 1H), 7.88 (dd, J=8.4, 1.4 Hz, 1H), 7.59 (dd, J=8.4, 0.6 Hz, 1H), 7.24 (s, 1H), 3.97 (s, 3H), 3.87 (s, 3H); LCMS (ESI) m/e 268.0 [(M–H)+, calcd $C_{11}H_{11}Br_1N_1O_2$, 268.0]; LC/MS retention time (method B): $t_R$=1.80 min.

INTERMEDIATE D

Methyl 3-iodo-1-methyl-1H-indole-6-carboxylate

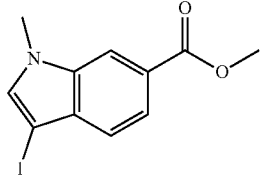

Prepared as described for intermediate C. Obtained title compound (3.61 g, 91% yield). $^1$H NMR (400 MHz, CHLOROFORM-d) δ 8.67-8.53 (s, 1H), 8.15 (d, J=0.8 Hz, 1H), 7.90 (dd, J=8.4, 1.4 Hz, 1H), 7.50 (d, J=8.5 Hz, 1H), 7.46 (d, J=2.8 Hz, 1H), 3.96 (s, 3H); $^1$H NMR (400 MHz, CHLOROFORM-d) δ 8.06 (d, J=0.8 Hz, 1H), 7.87 (dd, J=8.4, 1.4 Hz, 1H), 7.45 (d, J=8.0 Hz, 1H), 7.27 (s, 1H), 3.96 (s, 3H), 3.86 (s, 3H); LCMS (ESI) m/e 300.0 [(M–H)+, calcd $C_{10}H_7I_1N_1O_2$, 300.0]; LC/MS retention time (method B): $t_R$=1.71 min.

INTERMEDIATE E

3-Bromo-1-methyl-1H-indole-6-carboxylic Acid

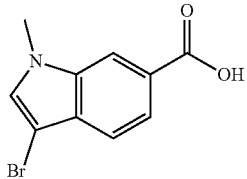

A mixture of LiOH (0.172 g, 7.20 mmol) and methyl 3-bromo-1-methyl-1H-indole-6-carboxylate (0.965 g, 3.60 mmol) in THF (4 mL), water (1.5 mL), and MeOH (1.5 mL) was stirred at room temperature for 24 hours. The volatiles were removed under vacuum and 1N HCl (6 mL) was added to the residue. The slurry was filtered and the solid was collected via vacuum filtration and washed with water. The solid was taken up in ethyl acetate and dried with $Na_2SO_4$. The ethyl acetate layer was filtered and concentrated under reduced pressure to give the title product as a white solid (0.837 g, 92% yield). The material was carried forward without further purification. $^1$H NMR (400 MHz, CHLOROFORM-d) δ 8.17 (s, 1H), 7.93 (dd, J=8.3, 1.3 Hz, 1H), 7.63 (d, J=8.5 Hz, 1H), 7.28 (s, 1H), 3.89 (s, 3H); LCMS (ESI) m/e 252.0 [(M–H)+, calcd $C_{10}H_7Br_1N_1O_2$, 251.9]; LC/MS retention time (method B): $t_R$=1.17 min.

INTERMEDIATE F

3-Bromo-1-methyl-N-(methylsulfonyl)-1H-indole-6-carboxamide

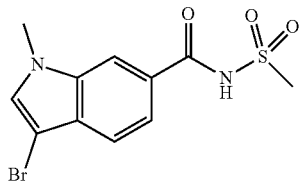

2-Chloro-1-methylpyridin-1-ium iodide (1.010 g, 3.95 mmol) was added to a solution of 3-bromo-1-methyl-1H-indole-6-carboxylic acid (0.837 g, 3.29 mmol) in $CH_2Cl_2$ (10 mL) at room temperature. The reaction was stirred at room temperature for 10 min before adding methanesulfonamide (0.940 g, 9.88 mmol). The reaction mixture was stirred at room temperature for 10 min then TEA (1.377 mL, 9.88 mmol) was slowly added. Heat generation was observed during this addition process. The reaction was allowed to stir at room temperature for 1 hour. The solvent was removed under vacuum and 1N HCl (3 mL) and water (20 mL) were added to the residue. The aqueous mixture was extracted with ethyl acetate three times. The ethyl acetate layers were combined, dried (Na$_2$SO$_4$), filtered and concentrated under reduced pressure. Methanol was added to the residue and a white suspension formed. The solid was filtered off and discarded. The filtrate was concentrated under reduced pressure to afford the title compound (1.02 g, 93% yield) which was carried forward without further purification. LCMS (ESI) m/e 329.2 [(M−H)$^+$, calcd C$_{11}$H$_{10}$Br$_1$N$_2$O$_3$S$_1$, 328.9]; LC/MS retention time (method B): t$_R$=1.21 min.

EXAMPLE 1

1-Methyl-N-(methylsulfonyl)-3-(4-(trifluoromethyl) phenyl)-1H-indole-6-carboxamide

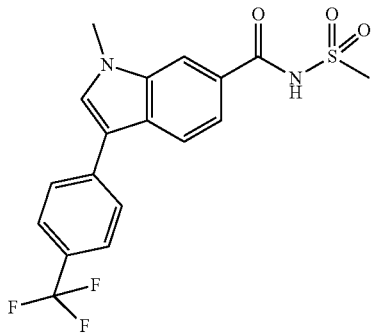 [SMILES: Cn1cc(-c2ccc(C(F)(F)F)cc2)c2ccc(C(=O)NS(C)(=O)=O)cc21]

Prepared following General Scheme I:

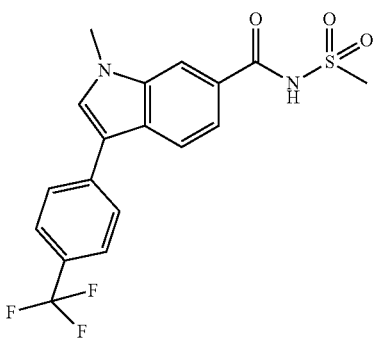 [SMILES: Cn1cc(-c2ccc(C(F)(F)F)cc2)c2ccc(C(=O)NS(C)(=O)=O)cc21]

A mixture of sodium carbonate (0.181 mL, 0.361 mmol), PdCl2(dppf) (3.30 mg, 4.51 μmol), (4-(trifluoromethyl)phenyl)boronic acid (0.017 g, 0.090 mmol) and 3-bromo-1-methyl-N-(methylsulfonyl)-1H-indole-6-carboxamide, intermediate F (0.0299 g, 0.090 mmol) in dioxane (0.5 mL) was heated at 100° C. for 2 hours. The crude material was purified via preparative LC/MS with the following conditions: Column: XBridge C18, 19×200 mm, 5-m particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min. Fractions containing the desired product were combined and dried via centrifugal evaporation. Obtained titled product (7 mg, 18% yield). $^1$H NMR (500 MHz, DMSO-d6) δ 8.31 (s, 1H), 8.14 (s, 1H), 8.03 (d, J=8.4 Hz, 1H), 7.93 (d, J=8.1 Hz, 2H), 7.79 (d, J=8.1 Hz, 3H), 3.95 (s, 3H), 2.55 (s, 3H); LCMS (ESI) m/e 397.1 [(M+H)$^+$, calcd C$_{18}$H$_{16}$F$_3$N$_2$O$_3$S$_1$, 397.1]; LC/MS retention time (method B): t$_R$=2.16 min.

EXAMPLE 2

3-(5-Chloro-6-isobutoxypyridin-3-yl)-1-methyl-N-(methylsulfonyl)-1H-indole-6-carboxamide

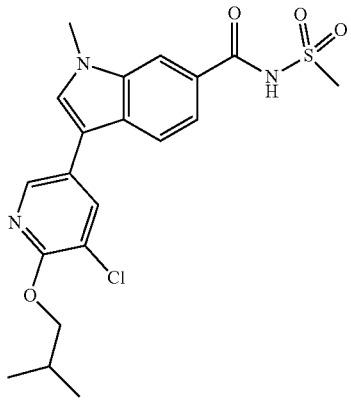

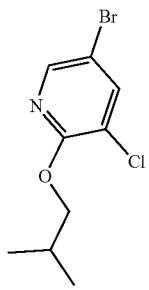

Part A: 5-Bromo-3-chloro-2-isobutoxypyridine

A mixture of cesium carbonate (1.124 g, 3.45 mmol), 5-bromo-3-chloro-2-fluoropyridine (0.2420 g, 1.150 mmol) and 2-methylpropan-1-ol (0.256 g, 3.45 mmol) in DMSO (5 mL) was stirred at 80° C. for 3 hours. The reaction mixture was cooled to room temperature then was diluted with water and extract with diethyl ether three times. The diethyl ether layers were combined, dried (Na2SO4), filtered and concentrated. The residue was purified via silica gel flash column chromatography eluting with ethyl acetate in hexane from 0-10% to give the desired product (0.222 g, 73% yield). $^1$H NMR (400 MHz, CHLOROFORM-d) δ 8.07 (d, J=2.3 Hz, 1H), 7.75 (d, J=2.3 Hz, 1H), 4.12 (d, J=6.5 Hz, 2H), 2.14 (dt, J=13.4, 6.7 Hz, 1H), 1.04 (d, J=6.8 Hz, 6H); LCMS (ESI) m/e 210.0 [(M-isobutyl)+, calcd C$_5$H$_3$Br$_1$Cl$_1$N$_1$O$_1$, 210.9]; LC/MS retention time (method B): t$_R$=2.58 min.

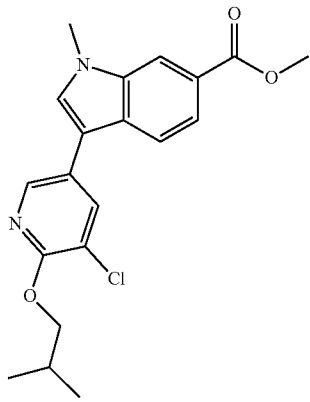 [SMILES: COC(=O)c1ccc2c(-c3cnc(OCC(C)C)c(Cl)c3)cn(C)c2c1]

Part B: Methyl 3-(5-chloro-6-isobutoxypyridin-3-yl)-1-methyl-1H-indole-6-carboxylate Tetrakis(triphenylphosphine)palladium (0) (0.065 g, 0.056 mmol) and methyl 3-iodo-1-methyl-1H-indole-6-carboxylate (0.5921 g, 1.879 mmol) in 1,4-dioxane (7.5 mL) in a pressure vial was subjected to vacuum/N2 fill three times. TEA (2.62 mL, 18.79 mmol) and 4,4,5,5-tetramethyl-1,3,2-dioxaborolane (0.409 mL, 2.82 mmol) were slowly added to the reaction mixture (bubbling observed). The reaction was then heated at 80° C. for 2 hours. TLC showed almost all the starting material was consumed. The reaction was cooled to room temperature. Methanol (1.5 mL) was added to the reaction mixture (violate gas evolution observed from decomposition of pinacolborane). 5-Bromo-3-chloro-2-isobutoxypyridine (0.497 g, 1.879 mmol) and cesium carbonate (1.53 g, 4.70 mmol) were added to the reaction mixture. The reaction was heated at 80° C. for 4 hours. The reaction was filtered and the solids washed with ethyl acetate. The filtrate was concentrated and the crude residue was purified via silica gel flash column chromatography eluting with ethyl acetate in hexane from 0 to 25% to 40% to obtain the title compound (0.36 g, 51% yield). $^1$H NMR (400 MHz, CHLOROFORM-d) δ 8.29 (d, J=2.3 Hz, 1H), 8.14 (s, 1H), 7.90-7.85 (m, 2H), 7.83-7.79 (m, 1H), 7.32 (s, 1H), 4.20 (d, J=6.8 Hz, 2H), 3.97 (s, 3H), 3.90 (s, 3H), 2.19 (dt, J=13.5, 6.7 Hz, 1H), 1.08 (d, J=6.5 Hz, 6H); LCMS (ESI) m/e 317.2 [(M+H-isobutyl)$^+$, calcd $C_{16}H_{14}C_{11}N_2O_3$, 317.1]; LC/MS retention time (method A): $t_R$=2.29 min.

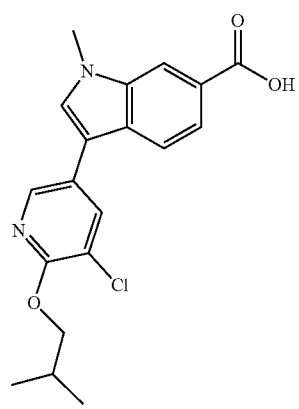 [SMILES: CC(C)COc1ncc(-c2cn(C)c3cc(C(=O)O)ccc23)cc1Cl]

Part C: 3-(5-Chloro-6-isobutoxypyridin-3-yl)-1-methyl-1H-indole-6-carboxylic Acid A mixture of LiOH (0.1002 g, 4.18 mmol) and methyl 3-(5-chloro-6-isobutoxypyridin-3-yl)-1-methyl-1H-indole-6-carboxylate (0.6776 g, 1.817 mmol) in THF (8 mL), water (3 mL) and MeOH (3 mL) was stirred at room temperature for 18 hours. The volatiles were removed under vacuum and 1N HCl (4.5 mL) was added to the residue. The material was diluted with water and extracted with ethyl acetate two times. The ethyl acetate layers were combined, dried with Na$_2$SO$_4$, filtered and concentrated to give the crude product as an off white solid (0.582 g, 89% yield). LCMS (ESI) m/e 357.2 [(M–H)$^+$, calcd $C_{19}H_{18}Cl_1N_2O_3$, 357.1]; LC/MS retention time (method A): $t_R$=1.69 min.

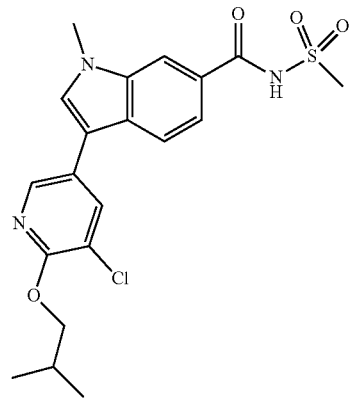 [SMILES: CC(C)COc1ncc(-c2cn(C)c3cc(C(=O)NS(C)(=O)=O)ccc23)cc1Cl]

Part D: 3-(5-Chloro-6-isobutoxypyridin-3-yl)-1-methyl-N-(methylsulfonyl)-1H-indole-6-carboxamide 2-Chloro-1-methylpyridin-1-ium iodide (0.259 g, 1.015 mmol) was added to a suspension of 3-(5-chloro-6-isobutoxypyridin-3-yl)-1-methyl-1H-indole-6-carboxylic acid (0.3035 g, 0.846 mmol) and DMAP (5.17 mg, 0.042 mmol) in CH$_2$Cl$_2$ (5 mL) at room temperature. The reaction was stirred at room temperature for 10 min before adding methanesulfonamide (0.241 g, 2.54 mmol). The reaction mixture was then stirred at room temperature for 10 min then TEA (0.354 mL, 2.54 mmol) was added. The reaction stirring was continued at room temperature for 1 hour. The solvent was removed under reduced pressure. 1N HCl (1.5 mL) was added to the residue followed by water. The mixture was extracted with ethyl acetate three times. The ethyl acetate layers were combined, dried (Na$_2$SO$_4$), filtered and concentrated. The residue was purified via silica gel flash column chromatography eluting with methanol in CH2Cl2 from 0 to 5% to 10% to give the title product. The material was further purified by preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min. Fractions containing the desired product were combined and dried via centrifugal evaporation. Obtained the titled product (13.0 mg, 20% yield). $^1$H NMR (400 MHz, DMSO-d6) δ 12.00 (br. s., 1H), 8.43 (d, J=2.0 Hz, 1H), 8.30 (d, J=1.3 Hz, 1H), 8.14 (d, J=2.0 Hz, 1H), 8.03 (s, 1H), 7.93

(d, J=8.5 Hz, 1H), 7.74 (dd, J=8.4, 1.6 Hz, 1H), 4.17 (d, J=6.5 Hz, 2H), 3.92 (s, 3H), 3.40 (s, 3H), 2.09 (dt, J=13.4, 6.7 Hz, 1H), 1.01 (d, J=6.8 Hz, 6H); LCMS (ESI) m/e 458.1 [(M+Na)+, calcd $C_{20}H_{22}Cl_1N_3O_4S_1Na_1$, 458.1]; LC/MS retention time (method A): $t_R$=2.66 min.

EXAMPLE 3

3-(2,3-Difluorophenyl)-1-methyl-N-(methylsulfonyl)-1H-indole-6-carboxamide

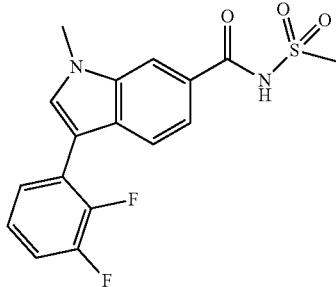 [SMILES: Cn1cc(-c2cccc(F)c2F)c2ccc(C(=O)NS(C)(=O)=O)cc21]

Prepared as described in Example 1 using intermediate F and (2,3-difluorophenyl)boronic acid. Obtained 4.7 mg, 15% yield. $^1$H NMR (500 MHz, DMSO-d6) δ 8.29 (s, 1H), 7.96 (s, 1H), 7.78-7.76 (m, 2H), 7.56-7.51 (m, 1H), 7.37-7.29 (m, 2H), 3.96 (s, 3H), 3.35-3.34 (s, 3H); $^{19}$F NMR (471 MHz, DMSO-d6) δ-138.59 (s, 1F), -141.82 (s, 1F); LCMS (ESI) m/e 363.2 [(M−H)+, calcd $C_{17}H_{13}F_2N_2O_3S_1$, 363.1]; LC/MS retention time (method A): $t_R$=1.32 min.

EXAMPLE 4

1-Methyl-N-(methylsulfonyl)-3-(4-(trifluoromethoxy)phenyl)-1H-indole-6-carboxamide

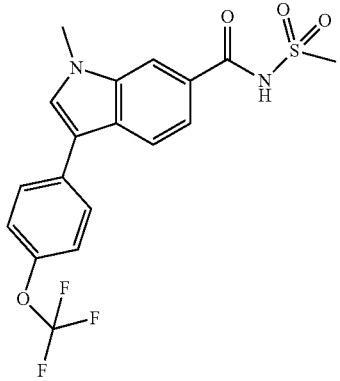 [SMILES: Cn1cc(-c2ccc(OC(F)(F)F)cc2)c2ccc(C(=O)NS(C)(=O)=O)cc21]

Prepared as described in Example 1 using intermediate F and (4-trifluoromethoxyphenyl)boronic acid. Obtained 2.2 mg, 5% yield. $^1$H NMR (500 MHz, DMSO-d6) δ 8.27 (s, 1H), 7.99 (s, 1H), 7.95 (d, J=8.4 Hz, 1H), 7.80 (d, J=8.4 Hz, 2H), 7.76 (d, J=8.4 Hz, 1H), 7.44 (d, J=8.8 Hz, 2H), 3.93 (s, 3H), 3.33-3.32 (m, 3H); $^{19}$F NMR (471 MHz, DMSO-d6) d −56.76 (s, 3F); LCMS (ESI) m/e 411.2 [(M−H)+, calcd $C_{18}H_{14}F_3N_2O_4S_1$, 411.1]; LC/MS retention time (method A): $t_R$=1.43 min.

EXAMPLE 5

1-Methyl-N-(methylsulfonyl)-3-phenyl-1H-indole-6-carboxamide

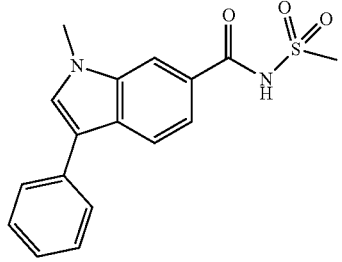 [SMILES: Cn1cc(-c2ccccc2)c2ccc(C(=O)NS(C)(=O)=O)cc21]

Prepared as described in Example 1 using intermediate F and 3-phenylboronic acid. Obtained 5.6 mg, 17% yield. $^1$H NMR (500 MHz, DMSO-d6) δ 8.26 (s, 1H), 7.96-7.92 (m, 2H), 7.74 (d, J=9.2 Hz, 1H), 7.69 (d, J=7.3 Hz, 2H), 7.46 (t, J=7.7 Hz, 2H), 7.27 (t, J=7.5 Hz, 1H), 3.93 (s, 3H), 3.34 (s, 3H); LCMS (ESI) m/e 327.3 [(M−H)+, calcd $C_{17}H_{15}N_2O_3S_1$, 327.1]; LC/MS retention time (method A): $t_R$=1.27 min.

EXAMPLE 6

3-(2-Methoxypyridin-3-yl)-1-methyl-N-(methylsulfonyl)-1H-indole-6-carboxamide

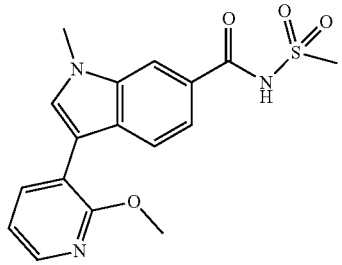 [SMILES: COc1ncccc1-c1cn(C)c2cc(C(=O)NS(C)(=O)=O)ccc12]

Prepared as described in Example 1 using intermediate F and (2-methoxypyridine-3)boronic acid. Obtained 6.2 mg, 15% yield. $^1$H NMR (500 MHz, DMSO-d6) δ 8.27 (s, 1H), 8.11 (dd, J=4.8, 1.8 Hz, 1H), 7.98 (dd, J=7.3, 1.8 Hz, 1H), 7.95 (s, 1H), 7.79-7.71 (m, 2H), 7.11 (dd, J=7.2, 5.0 Hz, 1H), 3.95 (s, 3H) 3.94 (s, 3H), 3.35 (br. s., 3H); LCMS (ESI) m/e 360.1 [(M+H)+, calcd $C_{17}H_{18}N_3O_4S_1$, 360.1]; LC/MS retention time (method D): $t_R$=1.45 min.

EXAMPLE 7

3-(5-Fluoropyridin-3-yl)-1-methyl-N-(methylsulfonyl)-1H-indole-6-carboxamide

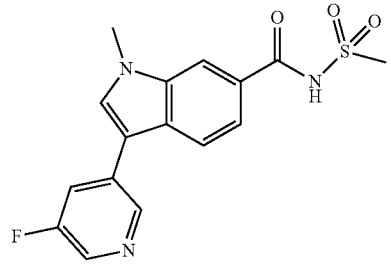 [SMILES: Cn1cc(-c2cncc(F)c2)c2ccc(C(=O)NS(C)(=O)=O)cc21]

Prepared as described in Example 1 using intermediate F and 3-fluoro-5-(4,4,5,5-tetramethyl-1,3,2-dioxaborolan-2-yl)pyridine. Obtained 4.1 mg, 8% yield. $^1$H NMR (500 MHz, DMSO-d6) δ 8.83 (s, 1H), 8.43 (d, J=2.9 Hz, 1H), 8.18 (s, 1H), 8.08 (s, 1H), 8.01-7.96 (m, 1H), 7.94-7.81 (m, 2H), 3.92 (s, 3H), 3.05 (s, 3H); $^{19}$F NMR (471 MHz, DMSO-d6) δ-127.44 (s, 1F)); LCMS (ESI) m/e 348.1 [(M+H)$^+$, calcd C$_{16}$H$_{15}$F$_1$N$_3$O$_3$S$_1$, 348.1]; LC/MS retention time (method D): t$_R$=1.16 min.

EXAMPLE 8

1-Methyl-N-(methylsulfonyl)-3-(pyridin-3-yl)-1H-indole-6-carboxamide

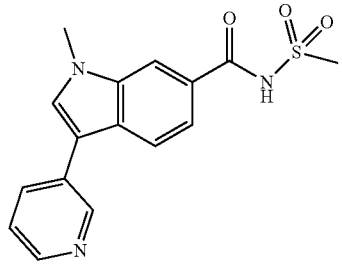 [SMILES: Cn1cc(-c2cccnc2)c2ccc(C(=O)NS(C)(=O)=O)cc21]

Prepared as described in Example 1 using intermediate F and pyridine-3-boronic acid. Obtained 8.4 mg, 38% yield. $^1$H NMR (500 MHz, DMSO-d6) δ 8.92 (s, 1H), 8.47 (d, J=4.6 Hz, 1H), 8.26 (s, 1H), 8.08 (d, J=7.9 Hz, 1H), 8.01 (s, 1H), 7.93 (d, J=8.2 Hz, 1H), 7.79 (d, J=8.9 Hz, 1H), 7.47 (dd, J=7.8, 4.7 Hz, 1H), 3.95 (s, 3H), 3.28 (s, 3H); LCMS (ESI) m/e 330.1 [(M+H)+, calcd C$_{16}$H$_{16}$N$_3$O$_3$S$_1$, 330.1]; LC/MS retention time (method D): t$_R$=0.93 min.

EXAMPLE 9

3-(2-Ethoxypyrimidin-5-yl)-1-methyl-N-(methylsulfonyl)-1H-indole-6-carboxamide

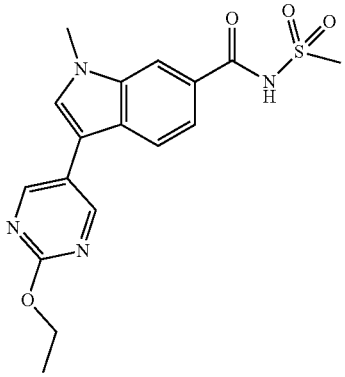 [SMILES: CCOc1ncc(-c2cn(C)c3cc(C(=O)NS(C)(=O)=O)ccc23)cn1]

Prepared as described in Example 1 using intermediate F and (2-ethoxypyrimidin-5-yl)boronic acid. Obtained 13.6 mg, 34% yield. $^1$H NMR (500 MHz, DMSO-d6) δ 8.91 (s, 2H), 8.28 (s, 1H), 8.02 (s, 1H), 7.91 (d, J=8.1 Hz, 1H), 7.76 (d, J=8.4 Hz, 1H), 4.41 (q, J=7.1 Hz, 2H), 3.93 (s, 3H), 3.32-3.31 (m, 3H), 1.38 (t, J=7.0 Hz, 3H); LCMS (ESI) m/e 375.1 [(M+H)$^+$, calcd C$_{17}$H$_{19}$N$_4$O$_4$S$_1$, 375.1]; LC/MS retention time (method D): t$_R$=1.40 min.

EXAMPLE 10

1-Methyl-N-(methylsulfonyl)-3-(p-tolyl)-1H-indole-6-carboxamide

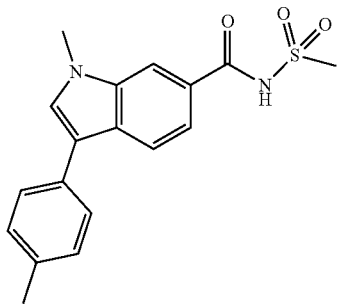 [SMILES: Cc1ccc(-c2cn(C)c3cc(C(=O)NS(C)(=O)=O)ccc23)cc1]

Prepared as described in Example 1 using intermediate F and p-tolylboronic acid. Obtained 4.9 mg, 13% yield. $^1$H NMR (500 MHz, DMSO-d6) δ 8.26 (s, 1H), 7.91 (d, J=1.0 Hz, 1H), 7.89 (s, 1H), 7.73 (d, J=8.4 Hz, 1H), 7.57 (d, J=8.1 Hz, 2H), 7.27 (d, J=8.1 Hz, 2H), 3.92 (s, 3H), 3.35 (br. s., 3H), 2.35 (s, 3H); LCMS (ESI) m/e 343.1 [(M+H)+, calcd C$_{18}$H$_{19}$N$_2$O$_3$S$_1$, 343.1]; LC/MS retention time (method D): t$_R$=1.87 min.

EXAMPLE 11

3-(2-Chloro-4-(trifluoromethyl)phenyl)-1-methyl-N-(methylsulfonyl)-1H-indole-6-carboxamide

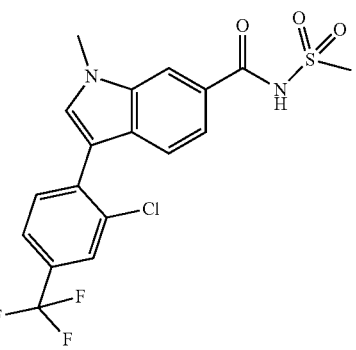

Prepared as described in Example 1 using intermediate F and (2-chloro-4-(trifluoromethyl)phenyl)boronic acid. Obtained 8.4 mg, 15% yield. $^1$H NMR (500 MHz, DMSO-d6) δ 8.33 (s, 1H), 8.02 (s, 1H), 8.00 (s, 1H), 7.81 (s, 2H), 7.76-7.72 (m, 1H), 7.63 (d, J=8.4 Hz, 1H), 3.98 (s, 3H), 3.40 (s, 3H); $^{19}$F NMR (471 MHz, DMSO-d6) d −60.97 (s, 3F); LCMS (ESI) m/e 431.0 [(M+H)$^+$, calcd C$_{18}$H$_{15}$Cl$_1$F$_3$N$_2$O$_3$S$_1$, 431.0]; LC/MS retention time (method D): t$_R$=2.10 min.

EXAMPLE 12

3-(4-Isobutylphenyl)-1-methyl-N-(methylsulfonyl)-1H-indole-6-carboxamide

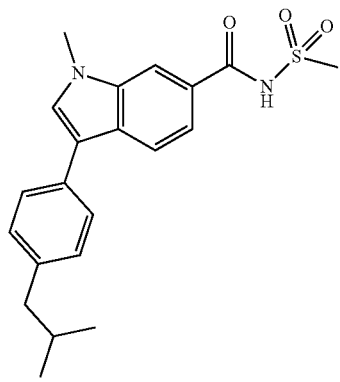 [SMILES: CC(C)Cc1ccc(-c2cn(C)c3cc(C(=O)NS(C)(=O)=O)ccc23)cc1]

Prepared as described in Example 1 using intermediate F and (4-isobutylphenyl)boronic acid. Obtained 7.7 mg, 20% yield. $^1$H NMR (500 MHz, DMSO-d6) δ 8.26 (s, 1H), 7.93 (d, J=8.4 Hz, 1H), 7.90 (s, 1H), 7.74 (d, J=8.4 Hz, 1H), 7.59 (d, J=8.1 Hz, 2H), 7.25 (d, J=8.1 Hz, 2H), 3.92 (s, 3H), 3.32 (s, 3H), 2.49 (d, J=6.6 Hz, 2H), 1.96-1.81 (sept, J=6.6 Hz, 1H), 0.91 (d, J=6.6 Hz, 6H); LCMS (ESI) m/e 385.1 [(M+H)$^+$, calcd $C_{21}H_{25}N_2O_3S_1$, 385.1]; LC/MS retention time (method D): $t_R$=2.28 min.

EXAMPLE 13

1-Methyl-N-(methylsulfonyl)-3-(3-(trifluoromethyl)phenyl)-1H-indole-6-carboxamide

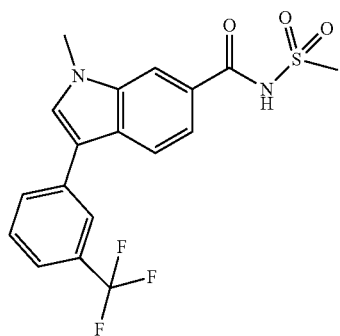 [SMILES: Cn1cc(-c2cccc(C(F)(F)F)c2)c2ccc(C(=O)NS(C)(=O)=O)cc21]

Prepared as described in Example 1 using intermediate F and (3-(trifluoromethyl)phenyl)boronic acid. Obtained 8.4 mg, 16% yield. $^1$H NMR (500 MHz, DMSO-d6) δ 8.30 (s, 1H), 8.15 (s, 1H), 8.03 (d, J=8.1 Hz, 1H), 7.98-7.92 (m, 2H), 7.79 (d, J=9.5 Hz, 1H), 7.70 (t, J=7.7 Hz, 1H), 7.61 (d, J=8.1 Hz, 1H), 3.95 (s, 3H), 3.33 (s, 3H); $^{19}$F NMR (471 MHz, DMSO-d6) d −61.09 (s, 3F); LCMS (ESI) m/e 397.0 [(M+H)+, calcd $C_{18}H_{16}F_3N_2O_3S_1$, 397.0]; LC/MS retention time (method D): $t_R$=1.91 min.

EXAMPLE 14

3-(4-Ethylphenyl)-1-methyl-N-(methylsulfonyl)-1H-indole-6-carboxamide

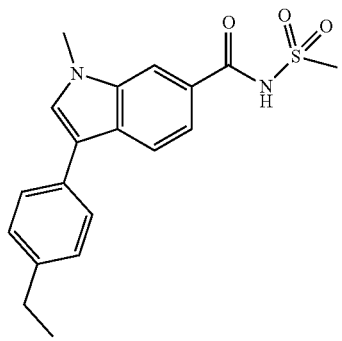 [SMILES: CCc1ccc(-c2cn(C)c3cc(C(=O)NS(C)(=O)=O)ccc23)cc1]

Prepared as described in Example 1 using intermediate F and (4-ethylphenyl)boronic acid. Obtained 3.8 mg, 11% yield. $^1$H NMR (500 MHz, DMSO-d6) δ 8.28 (s, 1H), 7.94 (d, J=8.4 Hz, 1H), 7.91 (s, 1H), 7.73 (d, J=8.4 Hz, 1H), 7.59 (d, J=8.1 Hz, 2H), 7.30 (d, J=8.1 Hz, 2H), 3.93 (s, 3H), 3.39 (s, 3H), 2.69-2.62 (m, 2H), 1.23 (t, J=7.5 Hz, 3H); LCMS (ESI) m/e 357.1 [(M+H)$^+$, calcd $C_{19}H_{21}N_2O_3S_1$, 357.1]; LC/MS retention time (method D): $t_R$=1.95 min.

EXAMPLE 15

1-Methyl-N-(methylsulfonyl)-3-(m-tolyl)-1H-indole-6-carboxamide

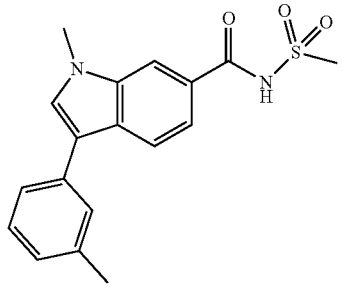 [SMILES: Cc1cccc(-c2cn(C)c3cc(C(=O)NS(C)(=O)=O)ccc23)c1]

Prepared as described in Example 1 using intermediate F and m-tolylboronic acid. Obtained 6.0 mg, 17% yield. $^1$H NMR (500 MHz, DMSO-d6) δ 8.25 (s, 1H), 7.93 (d, J=8.1 Hz, 1H), 7.91 (s, 1H), 7.74 (d, J=8.4 Hz, 1H), 7.50 (s, 1H), 7.48 (d, J=8.1 Hz, 1H), 7.34 (t, J=7.5 Hz, 1H), 7.09 (d, J=8.1 Hz, 1H), 3.92 (s, 3H), 3.31-3.30 (m, 3H), 2.39 (s, 3H); LCMS (ESI) m/e 343.0 [(M+H)+, calcd $C_{18}H_{19}N_2O_3S_1$, 343.1]; LC/MS retention time (method D): $t_R$=1.86 min.

EXAMPLE 16

3-(3-Isopropylphenyl)-1-methyl-N-(methylsulfonyl)-1H-indole-6-carboxamide

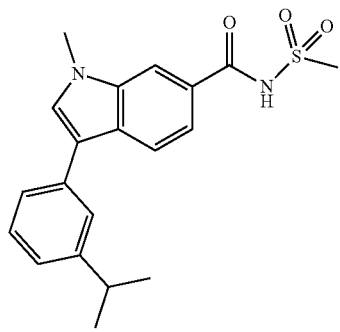 [SMILES: CC(C)c1cccc(-c2cn(C)c3cc(C(=O)NS(C)(=O)=O)ccc23)c1]

Prepared as described in Example 1 using intermediate F and (3-isopropylphenyl)boronic acid. Obtained 9.0 mg, 19% yield. $^1$H NMR (500 MHz, DMSO-d6) δ 8.28-8.25 (m, 1H), 7.94-7.90 (m, 2H), 7.74 (d, J=8.4 Hz, 1H), 7.52 (s, 1H), 7.49 (d, J=7.7 Hz, 1H), 7.40-7.35 (m, 1H), 7.16 (d, J=7.3 Hz, 1H), 3.93 (s, 3H), 3.31-3.30 (m, 3H), 2.99-2.94 (m, 1H), 1.28 (d, J=7.0 Hz, 6H); LCMS (ESI) m/e 371.1 [(M+H)$^+$, calcd $C_{20}H_{23}N_2O_3S_1$, 371.1]; LC/MS retention time (method D): $t_R$=2.05 min.

EXAMPLE 17

3-(3-Ethylphenyl)-1-methyl-N-(methylsulfonyl)-1H-indole-6-carboxamide

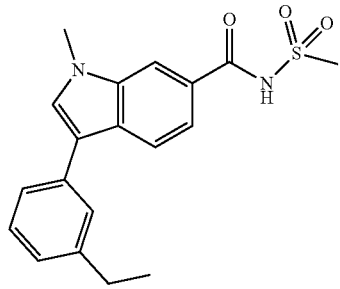 [SMILES: CCc1cccc(-c2cn(C)c3cc(C(=O)NS(C)(=O)=O)ccc23)c1]

Prepared as described in Example 1 using intermediate F and (3-ethylphenyl)boronic acid. Obtained 4.5 mg, 13% yield. $^1$H NMR (500 MHz, DMSO-d6) δ 8.29 (s, 1H), 7.98-7.94 (m, 2H), 7.73 (d, J=8.4 Hz, 1H), 7.52-7.48 (m, 2H), 7.37 (t, J=7.5 Hz, 1H), 7.15-7.10 (m, 1H), 3.93 (s, 3H), 3.41 (s, 3H), 2.69 (q, J=7.5 Hz, 2H), 1.25 (t, J=7.5 Hz, 3H); LCMS (ESI) m/e 357.0 [(M+H)$^+$, calcd $C_{19}H_{20}N_2O_3S_1$, 357.1]; LC/MS retention time (method D): $t_R$=1.97 min.

EXAMPLE 18

N-(cyclopropylsulfonyl)-1-methyl-3-(4-(trifluoromethyl)phenyl)-1H-indole-6-carboxamide

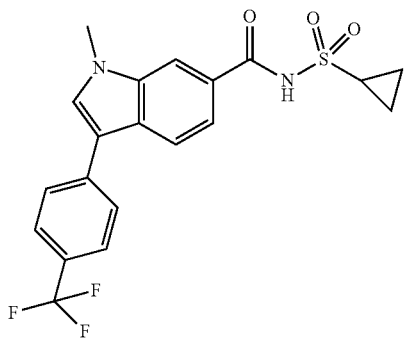 [SMILES: Cn1cc(-c2ccc(C(F)(F)F)cc2)c2ccc(C(=O)NS(=O)(=O)C3CC3)cc21]

Prepared following General Scheme II:

Part A: Methyl 1-methyl-3-(4-(trifluoromethyl)phenyl)-1H-indole-6-carboxylate Tetrakis(triphenylphosphine)palladium (0) (0.012 g, 10.12 μmol) and methyl 3-iodo-1-methyl-1H-indole-6-carboxylate (Compound D, 0.1063 g, 0.337 mmol) in 1,4-dioxane (1.5 mL) in a pressure vial was subjected to vacuum/N2 fill three times. TEA (0.470 mL, 3.37 mmol) and 4,4,5,5-tetramethyl-1,3,2-dioxaborolane (0.073 mL, 0.506 mmol) was added to the reaction mixture and the reaction was heated at 80° C. for 2 hours. The reaction was cooled to room temperature. Methanol (1.5 mL) was added to the reaction mixture (violate gas evolution observed from decomposition of pinacolborane). 1-Bromo-4-(trifluoromethyl)benzene (0.047 mL, 0.337 mmol) and cesium carbonate (0.275 g, 0.843 mmol) were added to the reaction mixture. The reaction was heated at 80° C. for 4 hours. The reaction was cooled to room temperature and the volatiles was removed under vacuum. The residue was purified via silica gel flash column chromatography eluting with ethyl acetate in hexane from 0 to 25% to 40%. The desired product is white solid which is a bright blue spot with Rf~0.3 in 25% ethyl acetate in hexane under UV (254 nm). Obtained 67.0 mg, 60% yield. $^1$H NMR (400 MHz, CHLOROFORM-d) δ 8.17 (s, 1H), 7.95-7.88 (m, 2H), 7.78-7.68 (m, 4H), 7.46 (s, 1H), 3.99 (s, 3H), 3.94 (s, 3H); $^{19}$F NMR (376 MHz, CHLOROFORM-d) 6-62.31 (s, 3F); LCMS (ESI) m/e 334.2

[(M+H)⁺, calcd C₁₈H₁₅F₃N₁₀O₂, 334.1]; LC/MS retention time (method A): $t_R$=2.03 min.

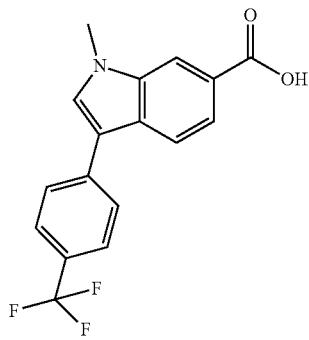 [SMILES: Cn1cc(-c2ccc(C(F)(F)F)cc2)c2ccc(C(=O)O)cc21]

Part B: 1-Methyl-3-(4-(trifluoromethyl)phenyl)-1H-indole-6-carboxylic Acid

A mixture of LiOH (13.6 mg, 0.568 mmol) and methyl 1-methyl-3-(4-(trifluoromethyl)phenyl)-1H-indole-6-carboxylate (0.067 g, 0.201 mmol) in THF (1 mL), water (0.2 mL) and MeOH (0.5 mL) at room temperature overnight. The volatiles were removed under vacuum and to the crude residue was added 1N HCl (0.6 mL). The solution was extracted with ethyl acetate two times. The ethyl acetate layers were combined, dried with Na₂SO₄, filtered and concentrated to give the crude product as a white solid. ¹H NMR (500 MHz, DMSO-d6) δ 8.15 (s, 1H), 8.09 (s, 1H), 7.99 (d, J=8.4 Hz, 1H), 7.92 (d, J=8.1 Hz, 2H), 7.81-7.77 (m, 3H), 3.94 (s, 3H); LCMS (ESI) me 320.1 [(M+H)⁺, calcd C₁₇H₁₃F₃N₁O₂, 320.1]; LC/MS retention time (method D): $t_R$=1.98 min.

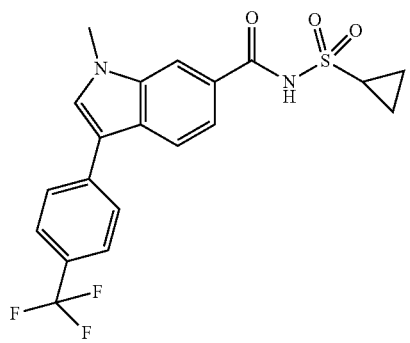 [SMILES: Cn1cc(-c2ccc(C(F)(F)F)cc2)c2ccc(C(=O)NS(=O)(=O)C3CC3)cc21]

Part C: N-(cyclopropylsulfonyl)-1-methyl-3-(4-(trifluoromethyl)phenyl)-1H-indole-6-carboxamide Followed the coupling procedure in Example 2 to make acyl sulfonamide, using cyclopropanesulfonamide. Obtained 6.9 mg, 44% yield. ¹H NMR (500 MHz, DMSO-d6) δ 12.00 (br. s., 1H), 8.31 (s, 1H), 8.16 (s, 1H), 8.04 (d, J=8.4 Hz, 1H), 7.93 (d, J=8.1 Hz, 2H), 7.81-7.75 (m, 3H), 3.96 (s, 3H), 3.22-3.15 (m, 1H), 1.21-1.10 (m, 4H); ¹⁹F NMR (471 MHz, DMSO-d6) δ-60.63 (s, 3F); LCMS (ESI) m/e 423.0 [(M+H)⁺, calcd C₂₀H₁₈F₃N₂O₃S₁, 423.1]; LC/MS retention time (method D): $t_R$=2.13 min.

EXAMPLE 19

1-Methyl-3-(4-(trifluoromethyl)phenyl)-N-((trifluoromethyl)sulfonyl)-1H-indole-6-carboxamide

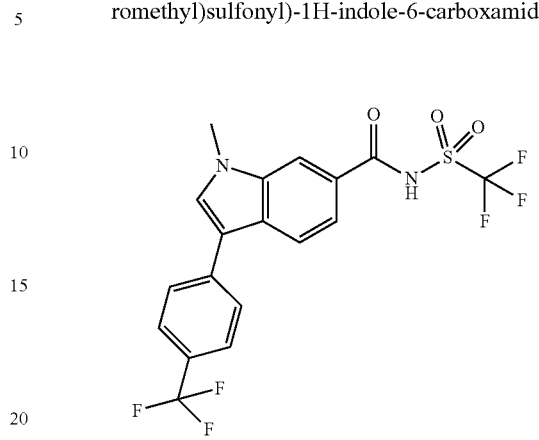

Prepared as described in Example 18 same using trifluoromethanesulfonamide. Obtained 9.1 mg, 61% yield. ¹H NMR (500 MHz, DMSO-d6) δ 8.11 (s, 1H), 8.01 (s, 1H), 7.94-7.89 (m, 3H), 7.83 (dd, J=8.4, 1.5 Hz, 1H), 7.77 (d, J=8.4 Hz, 2H), 3.92 (s, 3H); ¹⁹F NMR (471 MHz, DMSO-d6) δ-60.57 (s, 3F), -76.66 (s, 3F); LCMS (ESI) m/e 451.0 [(M+H)⁺, calcd C₁₈H₁₃F₆N₂O₃S₁, 451.0]; LC/MS retention time (method D): $t_R$=2.17 min.

EXAMPLE 20

1-Methyl-N-(thiophen-2-ylsulfonyl)-3-(4-(trifluoromethyl)phenyl)-1H-indole-6-carboxamide

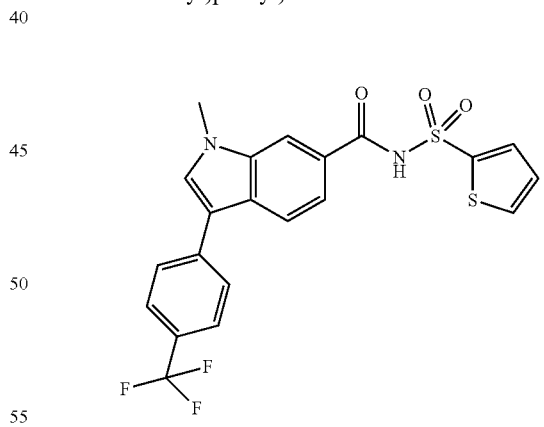

Prepared as described in Example 18 using thiophene-2-sulfonamide. Obtained 9.5 mg, 59% yield. ¹H NMR (500 MHz, DMSO-d6) δ 8.20 (s, 1H), 8.06 (s, 1H), 7.98-7.89 (m, 3H), 7.85-7.69 (m, 4H), 7.23-6.96 (m, 3H), 3.93 (s, 3H); ¹⁹F NMR (471 MHz, DMSO-d6) δ-60.60 (s, 3F); LCMS (ESI) m/e 465.0 [(M+H)⁺, calcd C₂₁H₁₆F₃N₂O₃S₂, 465.0]; LC/MS retention time (method D): $t_R$=2.25 min.

EXAMPLE 21

N-((3,4-difluorophenyl)sulfonyl)-1-methyl-3-(4-(trifluoromethyl)phenyl)-1H-indole-6-carboxamide

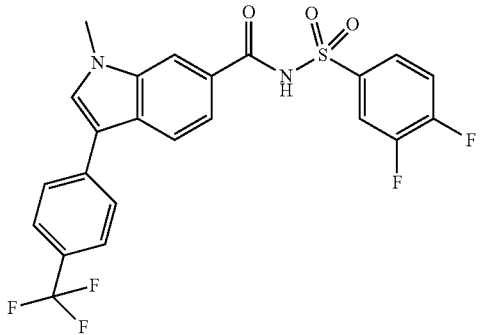 [SMILES: Cn1cc(-c2ccc(C(F)(F)F)cc2)c2ccc(C(=O)NS(=O)(=O)c3ccc(F)c(F)c3)cc21]

Prepared as described in Example 18 using 3,4-difluorobenzenesulfonamide. Obtained 7.7 mg, 49% yield. $^1$H NMR (500 MHz, DMSO-d6) δ 8.27 (s, 1H), 8.15 (s, 1H), 8.10-8.04 (m, 1H), 8.00 (d, J=8.8 Hz, 1H), 7.96-7.88 (m, 3H), 7.80-7.68 (m, 4H), 3.95 (s, 3H); LCMS (ESI) m/e 495.0 [(M+H)$^+$, calcd $C_{23}H_{16}F_5N_2O_3S_1$, 495.0]; LC/MS retention time (method D): $t_R$=2.39 min.

EXAMPLE 22

3-(4-Isobutoxyphenyl)-1-methyl-N-(methylsulfonyl)-1H-indole-6-carboxamide

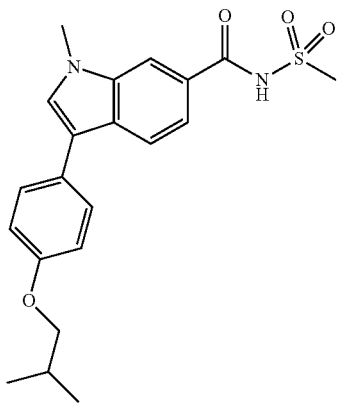 [SMILES: CC(C)COc1ccc(-c2cn(C)c3cc(C(=O)NS(C)(=O)=O)ccc23)cc1]

Prepared following General Scheme II:

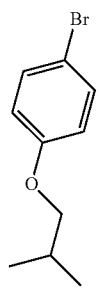

Part A: 1-Bromo-4-isobutoxybenzene

DIAD (1.911 mL, 9.83 mmol) was added dropwise to a solution of triphenylphosphine (2.58 g, 9.83 mmol), 4-bromophenol (1.5457 g, 8.93 mmol) and 2-methylpropan-1-ol (0.795 g, 10.72 mmol) in THF (30 mL) at 0° C. The reaction was stirred for 2 hours and the volatiles were removed under vacuum. The residue was purified via silica gel flash column chromatography eluting with ethyl acetate in hexane from 0 to 25%. The product was eluted out from solvent front as a clear oil (0.810 g, 40% yield). $^1$H NMR (400 MHz, CHLOROFORM-d) δ 7.40-7.34 (m, 2H), 6.81-6.76 (m, 2H), 3.69 (d, J=6.5 Hz, 2H), 2.14-2.02 (m, 1H), 1.03 (d, J=6.8 Hz, 6H).

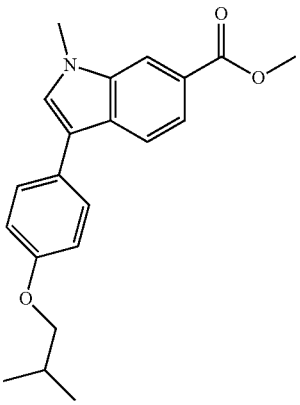 [SMILES: COC(=O)c1ccc2c(-c3ccc(OCC(C)C)cc3)cn(C)c2c1]

Part B: Methyl 3-(4-isobutoxyphenyl)-1-methyl-1H-indole-6-carboxylate

Followed the same Suzuki reaction procedure as in Example 18, Part A. Obtained 26 mg, 31% yield. LCMS (ESI) m/e 338.2 [(M+H)$^+$, calcd $C_{21}H_{24}N_1O_3$, 338.2]; LC/MS retention time (method A): $t_R$=2.15 min.

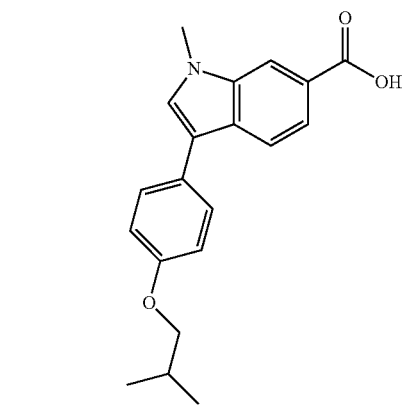 [SMILES: CC(C)COc1ccc(-c2cn(C)c3cc(C(=O)O)ccc23)cc1]

Part C: 3-(4-Isobutoxyphenyl)-1-methyl-1H-indole-6-carboxylic Acid

Followed the same hydrolysis reaction procedure as in Example 18, Part B. Obtained 22 mg, 88% yield. LCMS (ESI) m/e 324.1 [(M+H)$^+$, calcd $C_{20}H_{22}N_{10}O_3$, 324.2]; LC/MS retention time (method D): $t_R$=1.66 min.

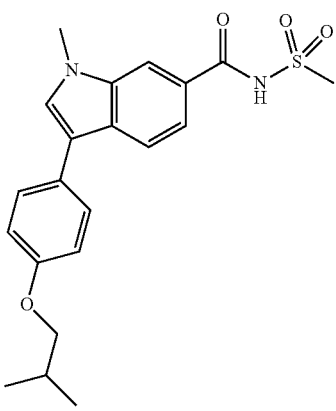 [SMILES: CC(C)COc1ccc(-c2cn(C)c3cc(C(=O)NS(C)(=O)=O)ccc23)cc1]

Part D: 3-(4-Isobutoxyphenyl)-1-methyl-N-(methylsulfonyl)-1H-indole-6-carboxamide Followed the same coupling procedure as described in Example 2, Part D. Obtained 7.6 mg, 28% yield. ¹H NMR (500 MHz, DMSO-d6) δ 11.98 (br. s., 1H), 8.26 (s, 1H), 7.89 (d, J=8.5 Hz, 1H), 7.84 (s, 1H), 7.74-7.71 (m, 1H), 7.58 (d, J=8.5 Hz, 2H), 7.03 (d, J=8.5 Hz, 2H), 3.91 (s, 3H), 3.79 (d, J=6.7 Hz, 2H), 3.36 (s, 3H), 2.05 (dt, J=13.5, 6.8 Hz, 1H), 1.01 (d, J=6.7 Hz, 6H); LCMS (ESI) m/e 401.1 [(M+H)⁺, calcd $C_{21}H_{25}F_5N_2O_4S_1$, 401.1]; LC/MS retention time (method D): $t_R$=2.12 min.

EXAMPLE 23

3-(6-Isobutoxypyridin-3-yl)-1-methyl-N-(methylsulfonyl)-1H-indole-6-carboxamide

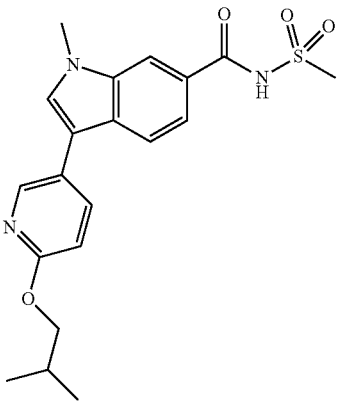 [SMILES: CC(C)COc1ccc(-c2cn(C)c3cc(C(=O)NS(C)(=O)=O)ccc23)cn1]

Prepared following General Scheme II:

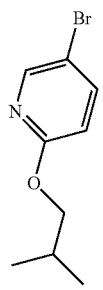

Part A: 5-Bromo-2-isobutoxypyridine

A mixture of cesium carbonate (1.977 g, 6.07 mmol), 5-bromo-2-fluoropyridine (1.07 g, 6.07 mmol) and 2-methylpropan-1-ol (0.899 g, 12.13 mmol) in DMSO (5 mL) was stirred at 120° C. for 18 hours. The reaction was diluted with water and extract with diethyl ether three times. The diethyl ether layers were combined, dried (Na2SO4), filtered and concentrated. The residue was purified via silica gel flash column chromatography eluting with ethyl acetate in hexane from 0 to 10% to give the desired product (1.20 g, 86% yield). ¹H NMR (400 MHz, CHLOROFORM-d) δ 8.21-8.15 (m, 1H), 7.64 (dd, J=8.8, 2.5 Hz, 1H), 6.66 (dd, J=8.8, 0.5 Hz, 1H), 4.03 (d, J=6.5 Hz, 2H), 2.08 (dt, J=13.4, 6.7 Hz, 1H), 1.01 (d, J=6.8 Hz, 6H); LCMS (ESI) m/e 173.9 [(M-isobutyl+H)⁺, calcd $C_5H_5Br_1N_1O_1$, 173.9]; LC/MS retention time (method A): $t_R$=2.01 min.

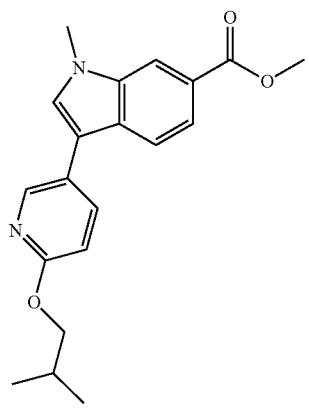 [SMILES: COC(=O)c1ccc2c(-c3ccc(OCC(C)C)nc3)cn(C)c2c1]

Part B: Methyl 3-(6-isobutoxypyridin-3-yl)-1-methyl-1H-indole-6-carboxylate

Followed the same Suzuki reaction procedure as in Example 18, Part A. Obtained 22.8 mg, 40% yield. ¹H NMR (400 MHz, CHLOROFORM-d) δ 8.42 (dd, J=2.5, 0.5 Hz, 1H), 8.16 (d, J=0.8 Hz, 1H), 7.90-7.80 (m, 3H), 7.33 (s, 1H), 6.85 (dd, J=8.5, 0.8 Hz, 1H), 4.13 (d, J=6.8 Hz, 2H), 3.98 (s, 3H), 3.93 (s, 3H), 2.14 (dt, J=13.5, 6.7 Hz, 1H), 1.06 (d, J=6.8 Hz, 6H); LCMS (ESI) m/e 339.2 [(M+H)⁺, calcd $C_{20}H_{23}N_2O_3$, 339.2]; LC/MS retention time (method A): $t_R$=2.06 min.

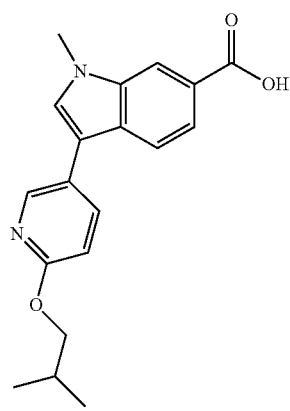 [SMILES: CC(C)COc1ccc(-c2cn(C)c3cc(C(=O)O)ccc23)cn1]

Part C: 3-(6-Isobutoxypyridin-3-yl)-1-methyl-1H-indole-6-carboxylic Acid

Followed the same hydrolysis reaction procedure as in Example 18, Part B. Obtained 18.5 mg, 85% yield. LCMS (ESI) m/e 325.2 [(M+H)+, calcd $C_{19}H_{21}N_2O_3$, 325.1]; LC/MS retention time (method A): $t_R$=1.49 min.

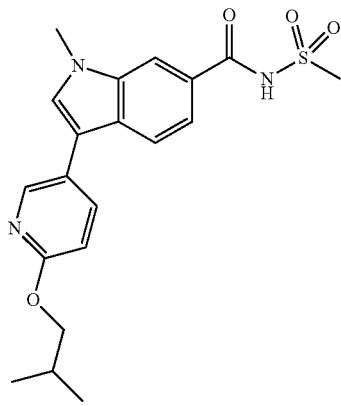 [SMILES: CC(C)COc1ccc(-c2cn(C)c3cc(C(=O)NS(C)(=O)=O)ccc23)cn1]

Part D: 3-(6-Isobutoxypyridin-3-yl)-1-methyl-N-(methylsulfonyl)-1H-indole-6-carboxamide Followed the same coupling reaction procedure as in Example 2, Part D. Obtained 12.3 mg, 54% yield. $^1$H NMR (500 MHz, DMSO-d6) δ 12.01 (br. s., 1H), 8.45 (d, J=2.4 Hz, 1H), 8.28 (s, 1H), 7.99 (dd, J=8.5, 2.7 Hz, 1H), 7.93 (s, 1H), 7.89 (d, J=8.5 Hz, 1H), 7.74 (dd, J=8.5, 1.5 Hz, 1H), 6.92 (d, J=8.5 Hz, 1H), 4.09 (d, J=6.4 Hz, 2H), 3.93 (s, 3H), 3.37 (s, 3H), 2.07 (dt, J=13.4, 6.7 Hz, 1H), 1.00 (d, J=6.7 Hz, 6H); LCMS (ESI) m/e 402.1 [(M+H)+, calcd $C_{20}H_{24}N_3O_4S_1$, 402.1]; LC/MS retention time (method D): $t_R$=1.69 min.

EXAMPLE 24

3-(5-Chloro-6-isobutoxypyridin-3-yl)-N-(cyclopropylsulfonyl)-1-methyl-1H-indole-6-carboxamide

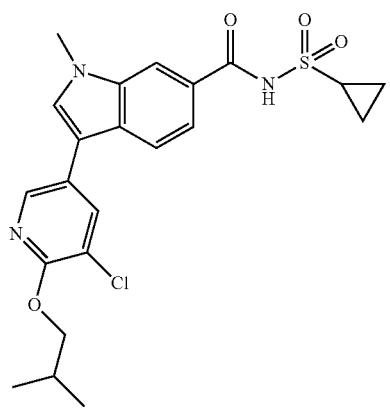 [SMILES: CC(C)COc1ncc(-c2cn(C)c3cc(C(=O)NS(=O)(=O)C4CC4)ccc23)cc1Cl]

Prepared as described in Example 2, Part D, using intermediate 3-(5-Chloro-6-isobutoxypyridin-3-yl)-1-methyl-1H-indole-6-carboxylic acid and cyclopropanesulfonamide.

Obtained 17.0 mg, 87% yield. 1H NMR (500 MHz, DMSO-d6) δ 8.44 (d, J=2.1 Hz, 1H), 8.24 (s, 1H), 8.15 (d, J=2.1 Hz, 1H), 7.99 (s, 1H), 7.89 (d, J=8.2 Hz, 1H), 7.76 (dd, J=8.5, 1.5 Hz, 1H), 4.18 (d, J=6.4 Hz, 2H), 3.92 (s, 3H), 3.18-3.11 (m, 1H), 2.10 (dt, J=13.4, 6.6 Hz, 1H), 1.10 (br. s., 2H), 1.02 (d, J=6.7 Hz, 8H, two cyclpropyl protons overlap with six isopropyl protons); LCMS (ESI) m/e 462.0 [(M+H)+, calcd $C_{22}H_{25}Cl_1N_3O_4S_1$, 462.1]; LC/MS retention time (method D): $t_R$=1.88 min.

EXAMPLE 25

3-(5-Chloro-6-isobutoxypyridin-3-yl)-N—(N,N-dimethylsulfamoyl)-1-methyl-1H-indole-6-carboxamide

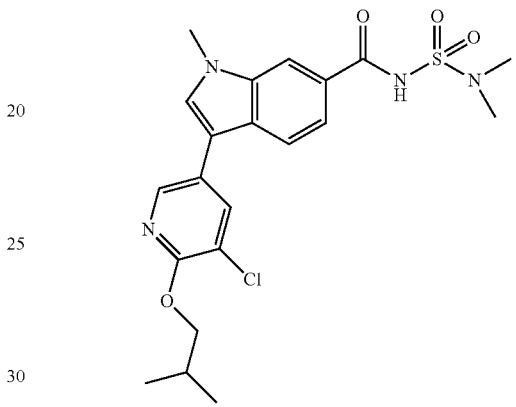

Prepared as described in Example 2, Part D, using intermediate 3-(5-chloro-6-isobutoxypyridin-3-yl)-1-methyl-1H-indole-6-carboxylic acid and sulfamide of dimethylsulfamic acid. Obtained 14.0 mg, 78% yield. $^1$H NMR (500 MHz, DMSO-d6) δ 11.72 (s, 1H), 8.44 (d, J=2.1 Hz, 1H), 8.30 (s, 1H), 8.15 (d, J=2.1 Hz, 1H), 8.03 (s, 1H), 7.93 (d, J=8.5 Hz, 1H), 7.74 (dd, J=8.5, 1.2 Hz, 1H), 4.18 (d, J=6.4 Hz, 2H), 3.93 (s, 3H), 2.93 (s, 6H), 2.10 (dt, J=13.4, 6.6 Hz, 1H), 1.02 (d, J=6.7 Hz, 6H) LCMS (ESI) m/e 465.0 [(M+H)+, calcd $C_{21}H_{26}C_{11}N_4O_4S_1$, 465.0]; LC/MS retention time (method D): $t_R$=2.35 min.

EXAMPLE 26

3-(5-Chloro-6-isobutoxypyridin-3-yl)-1-methyl-N-(piperidin-1-ylsulfonyl)-1H-indole-6-carboxamide

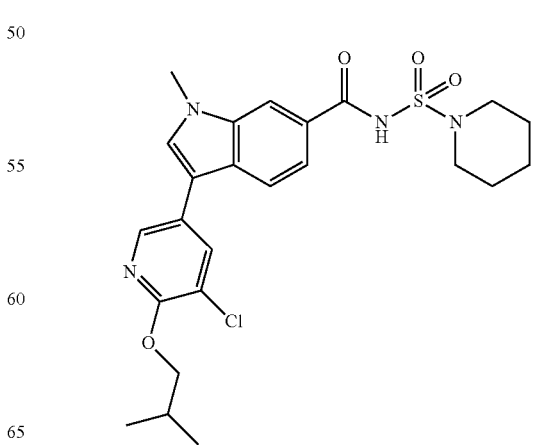

Prepared as described in Example 2, Part D, using intermediate 3-(5-Chloro-6-isobutoxypyridin-3-yl)-1-methyl-1H-indole-6-carboxylic acid and piperidine-1-sulfonamide. Obtained 13.5 mg, 65% yield. $^1$H NMR (500 MHz, DMSO-d6) δ 11.71 (s, 1H), 8.44 (d, J=2.1 Hz, 1H), 8.29 (s, 1H), 8.15 (d, J=2.1 Hz, 1H), 8.03 (s, 1H), 7.93 (d, J=8.5 Hz, 1H), 7.73 (d, J=8.5 Hz, 1H), 4.18 (d, J=6.7 Hz, 2H), 3.93 (s, 3H), 3.34 (m, 4H, under water peak), 2.10 (dt, J=13.3, 6.8 Hz, 1H), 1.58 (br. s., 4H), 1.50 (d, J=4.3 Hz, 2H), 1.02 (d, J=6.7 Hz, 6H); LCMS (ESI) m/e 505.0 [(M+H)$^+$, calcd $C_{24}H_{30}C_{11}N_4O_4S_1$, 505.2]; LC/MS retention time (method D): $t_R$=2.51 min.

EXAMPLE 27

3-(5-Chloro-6-isobutoxypyridin-3-yl)-1-isobutyl-N-(methylsulfonyl)-1H-indole-6-carboxamide

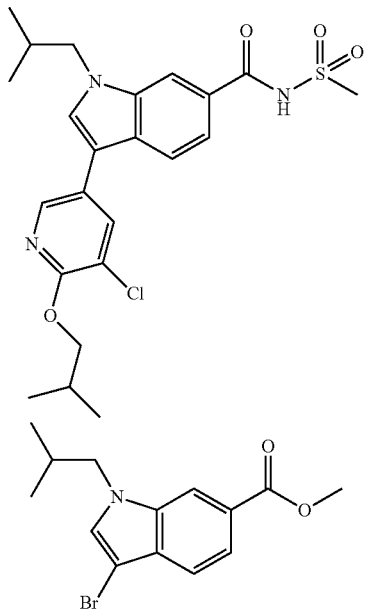

Part A: Methyl 3-bromo-1-isobutyl-1H-indole-6-carboxylate

Potassium carbonate (0.973 g, 7.04 mmol) was added to a solution of methyl 3-bromo-1H-indole-6-carboxylate (0.5960 g, 2.346 mmol) in DMF (5 mL) at room temperature. The mixture was stirred at room temperature for 30 min. The reaction was cooled to 0° C. and 1-iodo-2-methylpropane (0.324 mL, 2.81 mmol) was added to the reaction mixture. The reaction was stirred overnight while it warmed up to room temperature. The reaction was diluted with water and extracted three times with diethyl ether. The diethyl ether layers were combined, washed with NaCl (sat.) one time and dried (Na$_2$SO$_4$), filtered and concentrated. The residue was purified via silica gel flash column chromatography eluting with ethyl acetate in hexane from 0 to 25% to obtain the title compound as an off white solid (0.319 g, 44% yield). $^1$H NMR (400 MHz, CHLOROFORM-d) δ 8.09 (d, J=0.5 Hz, 1H), 7.86 (dd, J=8.4, 1.4 Hz, 1H), 7.60-7.57 (m, 1H), 7.25 (s, 1H), 3.96 (s, 3H), 3.95 (d, J=7.3 Hz, 2H), 2.20 (dt, J=13.6, 7.0 Hz, 1H), 0.94 (d, J=6.5 Hz, 6H); LCMS (ESI) m/e 309.2 [(M+H)$^+$, calcd $C_{14}H_{17}Br_1N_1O_2$, 309.0]; LC/MS retention time (method A): $t_R$=2.06 min.

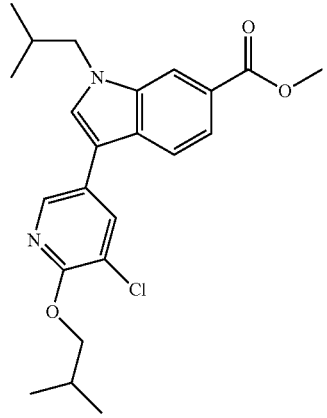 [SMILES: COC(=O)c1ccc2c(-c3cnc(OCC(C)C)c(Cl)c3)cn(CC(C)C)c2c1]

Part B: Methyl 3-(5-chloro-6-isobutoxypyridin-3-yl)-1-isobutyl-1H-indole-6-carboxylate Prepared as described in Example 18, Part A. Obtained 0.047 g, 23% yield. $^1$H NMR (400 MHz, CHLOROFORM-d) δ 8.31 (d, J=2.3 Hz, 1H), 8.15 (d, J=0.5 Hz, 1H), 7.90-7.81 (m, 3H), 7.36 (s, 1H), 4.21 (d, J=6.8 Hz, 2H), 4.03 (d, J=7.5 Hz, 2H), 3.98 (s, 3H), 2.28 (dt, J=13.5, 6.7 Hz, 1H), 2.19 (dt, J=13.5, 6.7 Hz, 1H), 1.08 (d, J=6.8 Hz, 6H), 0.99 (d, J=6.5 Hz, 6H); LCMS (ESI) m/e 415.2 [(M+H)$^+$, calcd $C_{23}H_{28}C_{11}N_2O_3$, 415.2]; LC/MS retention time (method A): $t_R$=2.15 min.

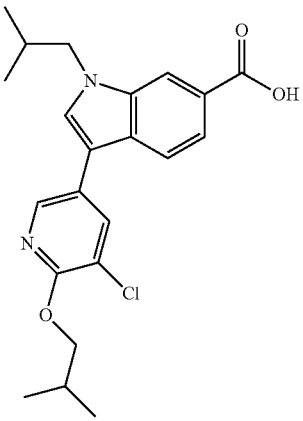 [SMILES: CC(C)COc1ncc(-c2cn(CC(C)C)c3cc(C(=O)O)ccc23)cc1Cl]

Part C: 3-(5-Chloro-6-isobutoxypyridin-3-yl)-1-isobutyl-1H-indole-6-carboxylic Acid Prepared as described in Example 18, Part B. Obtained 0.045 g, 99% yield. $^1$H NMR (400 MHz, CHLOROFORM-d) δ 8.31 (d, J=2.3 Hz, 1H), 8.15 (d, J=0.5 Hz, 1H), 7.90-7.81 (m, 3H), 7.36 (s, 1H), 4.21 (d, J=6.8 Hz, 2H), 4.03 (d, J=7.5 Hz, 2H), 3.98 (s, 3H), 2.28 (dt, J=13.5, 6.7 Hz, 1H), 2.19 (dt, J=13.5, 6.7 Hz, 1H), 1.08 (d, J=6.8 Hz, 6H), 0.99 (d, J=6.5 Hz, 6H); LCMS (ESI) m/e 401.1 [(M+H)$^+$, calcd $C_{22}H_{26}C_{11}N_2O_3$, 401.1]; LC/MS retention time (method A): $t_R$=1.92 min.

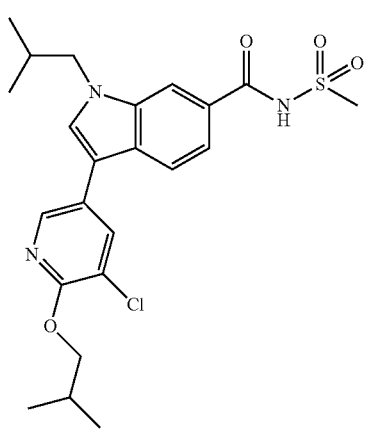 [SMILES: CC(C)COc1ncc(-c2cn(CC(C)C)c3cc(C(=O)NS(C)(=O)=O)ccc23)cc1Cl]

Part D: 3-(5-Chloro-6-isobutoxypyridin-3-yl)-1-isobutyl-N-(methylsulfonyl)-1H-indole-6-carboxamide Prepared as described in Example 2, Part D. Obtained 0.012 g, 96% yield. $^1$H NMR (500 MHz, DMSO-d6) δ 8.46 (d, J=2.1 Hz, 1H), 8.28 (s, 1H), 8.18 (d, J=2.1 Hz, 1H), 8.08 (s, 1H), 7.93 (d, J=8.5 Hz, 1H), 7.75 (dd, J=8.7, 1.4 Hz, 1H), 4.18 (d, J=6.7 Hz, 2H), 4.10 (d, J=7.3 Hz, 2H), 3.37 (s, 3H), 2.32-2.24 (m, 1H), 2.11 (dt, J=13.2, 6.7 Hz, 1H), 1.02 (d, J=6.7 Hz, 6H), 0.92 (d, J=6.7 Hz, 6H); LCMS (ESI) m/e 478.0 [(M+H)$^+$, calcd $C_{23}H_{29}C_{11}N_3O_4S_1$, 478.1]; LC/MS retention time (method D): $t_R$=2.48 min.

EXAMPLE 28

3-(5-Chloro-6-isobutoxypyridin-3-yl)-N-(cyclopropylsulfonyl)-1-isobutyl-1H-indole-6-carboxamide

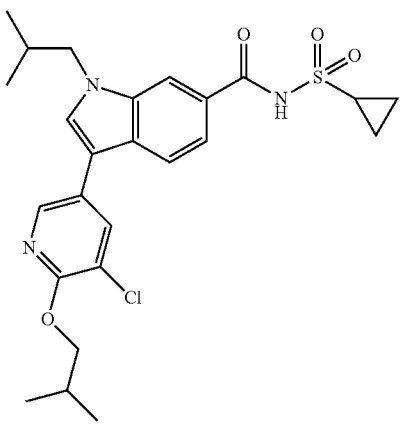 [SMILES: CC(C)COc1ncc(-c2cn(CC(C)C)c3cc(C(=O)NS(=O)(=O)C4CC4)ccc23)cc1Cl]

Prepared as described in Example 2, Part D using cyclopropanesulfonamide. Obtained 0.015 g, 17% yield. $^1$H NMR (500 MHz, DMSO-d6) δ 8.46 (d, J=2.1 Hz, 1H), 8.26 (s, 1H), 8.18 (d, J=2.1 Hz, 1H), 8.08 (s, 1H), 7.94 (d, J=8.5 Hz, 1H), 7.77-7.73 (m, 1H), 4.18 (d, J=6.7 Hz, 2H), 4.11 (d, J=7.3 Hz, 2H), 3.22-3.15 (m, 1H), 2.33-2.24 (m, 1H), 2.11 (dt, J=13.4, 6.7 Hz, 1H), 1.19-1.14 (m, 2H), 1.14-1.07 (m, J=6.4 Hz, 2H), 1.02 (d, J=6.7 Hz, 6H), 0.92 (d, J=6.7 Hz, 6H); LCMS (ESI) m/e 504.1 [(M+H)$^+$, calcd $C_{25}H_{31}C_{11}N_3O_4S_1$, 504.2]; LC/MS retention time (method D): $t_R$=2.19 min.

EXAMPLE 29

3-(5-Chloro-6-isobutoxypyridin-3-yl)-1-isopropyl-N-(methylsulfonyl)-1H-indole-6-carboxamide

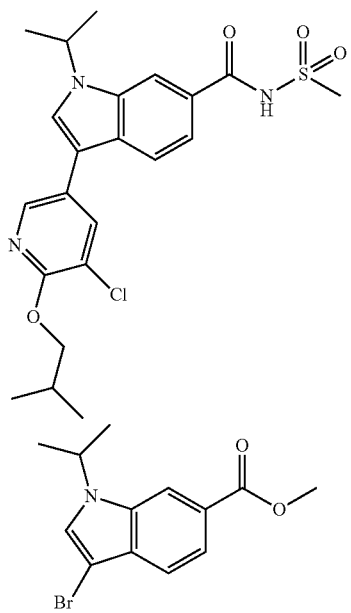

Part A: Methyl 3-bromo-1-isopropyl-1H-indole-6-carboxylate

Prepared as described in Example 27, Part A using 2-iodopropane. Obtained 0.342 g, 46% yield. $^1$H NMR (400 MHz, CHLOROFORM-d) δ 8.16 (s, 1H), 7.87 (dd, J=8.4, 1.4 Hz, 1H), 7.58 (dd, J=8.5, 0.5 Hz, 1H), 7.39 (s, 1H), 4.78 (dt, J=13.4, 6.7 Hz, 1H), 3.97 (s, 3H), 1.55 (d, J=6.8 Hz, 6H); LCMS (ESI) m/e 296.1 [(M+H)$^+$, calcd $C_{13}H_{15}Br_1N_1O_2$, 296.0]; LC/MS retention time (method A): $t_R$=1.98 min.

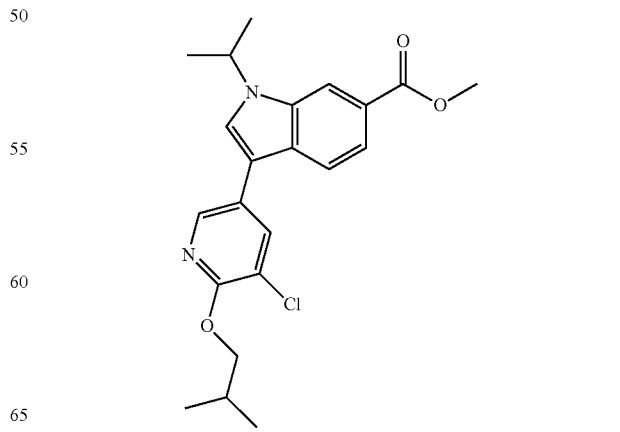

Part B: Methyl 3-(5-chloro-6-isobutoxypyridin-3-yl)-1-isopropyl-1H-indole-6-carboxylate Prepared as in Example 2, Part B. Obtained 0.059 g, 13% yield. $^1$H NMR (400 MHz, CHLOROFORM-d) δ 8.32 (d, J=2.0 Hz, 1H), 8.22 (s, 1H), 7.90-7.86 (m, 2H), 7.84-7.81 (m, 1H), 7.49 (s, 1H), 4.90-4.74 (m, 1H), 4.21 (d, J=6.8 Hz, 2H), 3.98 (s, 3H), 2.20 (dt, J=13.4, 6.7 Hz, 1H), 1.61 (d, J=6.8 Hz, 6H), 1.09 (d, J=6.8 Hz, 6H); LCMS (ESI) m/e 401.2 [(M+H)$^+$, calcd $C_{22}H_{26}Cl_1N_2O_3$, 401.2]; LC/MS retention time (method A): $t_R$=2.35 min.

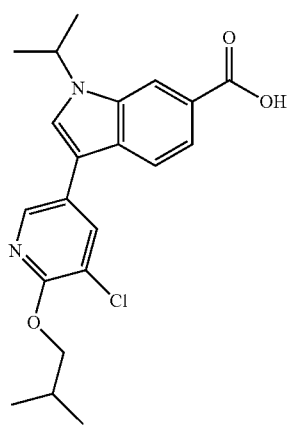 [SMILES: CC(C)COc1ncc(-c2cn(C(C)C)c3cc(C(=O)O)ccc23)cc1Cl]

Part C: 3-(5-Chloro-6-isobutoxypyridin-3-yl)-1-isopropyl-1H-indole-6-carboxylic Acid Prepared as in Example 18, Part B. Obtained 0.054 g, 73% yield, 77% purity. LCMS (ESI) m/e 331.1 [(M-isobutyl+H)$^+$, calcd $C_{17}H_{16}Cl_1N_2O_3$, 331.1]; LC/MS retention time (method A): $t_R$=1.84 min.

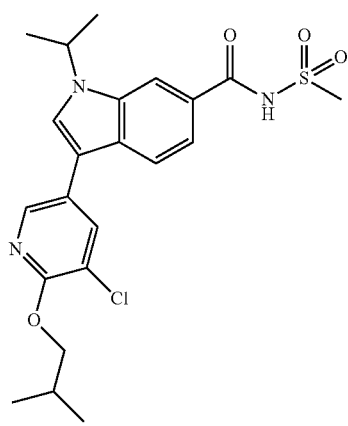 [SMILES: CC(C)COc1ncc(-c2cn(C(C)C)c3cc(C(=O)NS(C)(=O)=O)ccc23)cc1Cl]

Part D: 3-(5-Chloro-6-isobutoxypyridin-3-yl)-1-isopropyl-N-(methylsulfonyl)-1H-indole-6-carboxamide Prepared as in Example 2, Part D using mathanesulfonamide. Obtained 9.7 mg, 45% yield. $^1$H NMR (500 MHz, DMSO-d6) δ 8.47 (d, J=2.1 Hz, 1H), 8.34 (s, 1H), 8.20-8.17 (m, 2H), 7.91 (d, J=8.5 Hz, 1H), 7.76 (d, J=8.5 Hz, 1H), 4.91 (dt, J=13.4, 6.7 Hz, 1H), 4.21 (d, J=6.4 Hz, 2H), 3.37 (s, 3H), 2.12 (dt, J=13.4, 6.6 Hz, 1H), 1.58 (d, J=6.7 Hz, 6H), 1.03 (d, J=6.7 Hz, 6H); LCMS (ESI) m/e 464.0 [(M+H)$^+$, calcd $C_{22}H_{27}Cl_1N_3O_4S_1$, 464.1]; LC/MS retention time (method D): $t_R$=2.56 min.

EXAMPLE 30

3-(4-(Difluoromethyl)phenyl)-1-methyl-N-(methylsulfonyl)-1H-indole-6-carboxamide

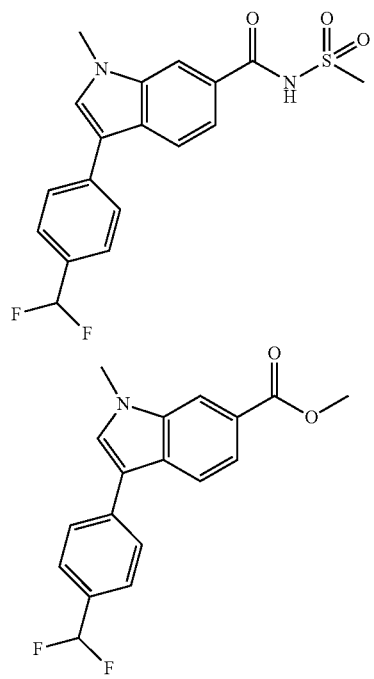

Part A: Methyl 3-(4-(difluoromethyl)phenyl)-1-methyl-1H-indole-6-carboxylate:

Prepared as in Example 2, Part B, using 1-bromo-4-(difluoromethyl)benzene Obtained 0.073 g, 63% yield. $^1$H NMR (400 MHz, CHLOROFORM-d) δ 8.15 (s, 1H), 7.95-7.87 (m, 2H), 7.71 (d, J=8.3 Hz, 2H), 7.58 (d, J=8.3 Hz, 2H), 7.40 (s, 1H), 6.71 (t, J=56.0 Hz, 1H), 3.98 (s, 3H), 3.89 (s, 3H); $^{19}$F NMR (376 MHz, CHLOROFORM-d) 6-109.86 (s, 2F); LCMS did not give ionization; LC/MS retention time (method A): $t_R$=1.98 min.

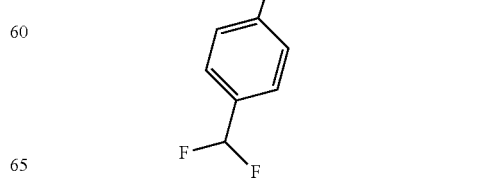

Part B: 3-(4-(Difluoromethyl)phenyl)-1-methyl-1H-indole-6-carboxylic Acid

Prepared as in Example 18, Part B. Obtained 0.062 g, 90% yield. LCMS (ESI) m/e 302.0 [(M+H)+, calcd $C_{17}H_{14}F_2N_{10}O_2$, 302.1]; LC/MS retention time (method A): $t_R$=1.39 min.

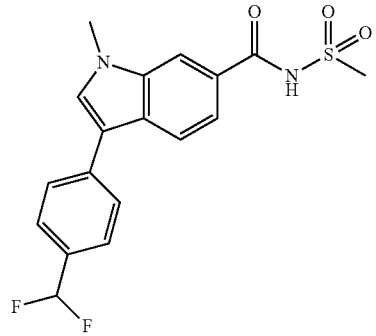 [SMILES: Cn1cc(-c2ccc(C(F)F)cc2)c2ccc(C(=O)NS(C)(=O)=O)cc21]

Part C: 3-(4-(Difluoromethyl)phenyl)-1-methyl-N-(methylsulfonyl)-1H-indole-6-carboxamide Prepared as in Example 2, Part D using mathanesulfonamide. Obtained 6.1 mg, 39% yield. $^1$H NMR (500 MHz, DMSO-d6) δ 8.30 (s, 1H), 8.08 (s, 1H), 8.02 (d, J=8.5 Hz, 1H), 7.84 (d, J=7.9 Hz, 2H), 7.77 (dd, J=8.7, 1.4 Hz, 1H), 7.65 (d, J=7.9 Hz, 2H), 7.06 (t, J=56.0 Hz, 1H), 3.95 (s, 3H), 3.40 (br. s., 3H); $^{19}$F NMR (471 MHz, DMSO-d6) d −108.62 (s, 2F); LCMS (ESI) m/e 379.0 [(M+H)+, calcd $C_{18}H_{17}F_2N_2O_3S_1$, 379.1]; LC/MS retention time (method D): $t_R$=1.71 min.

EXAMPLE 31

N-(cyclopropylsulfonyl)-3-(4-(difluoromethyl)phenyl)-1-methyl-1H-indole-6-carboxamide

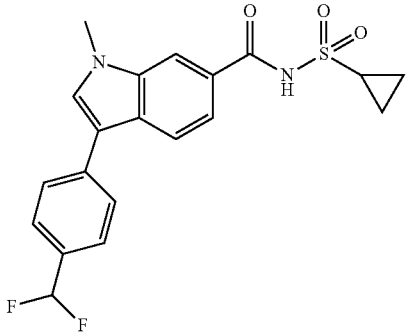 [SMILES: Cn1cc(-c2ccc(C(F)F)cc2)c2ccc(C(=O)NS(=O)(=O)C3CC3)cc21]

Prepared as in Example 30 using cyclopropanesulfonamide and intermediate acid from Example 30. Obtained 10.5 mg, 75% yield. $^1$H NMR (500 MHz, DMSO-d6) δ 11.99 (br. s., 1H), 8.29 (s, 1H), 8.08 (s, 1H), 8.02 (d, J=8.2 Hz, 1H), 7.84 (d, J=7.9 Hz, 2H), 7.77 (dd, J=8.5, 1.2 Hz, 1H), 7.65 (d, J=8.2 Hz, 2H), 7.06 (t, J=56.0 Hz, 1H), 3.95 (s, 3H), 3.22-3.14 (m, 1H), 1.20-1.09 (m, 4H); $^{19}$F NMR (471 MHz, DMSO-d6) δ-108.64 (s, 2F); LCMS (ESI) m/e 405.0 [(M+H)+, calcd $C_{20}H_{19}F_2N_2O_3S_1$, 405.1]; LC/MS retention time (method D): $t_R$=1.83 min.

EXAMPLE 32

3-(4-(Difluoromethyl)phenyl)-N—(N,N-dimethylsulfamoyl)-1-methyl-1H-indole-6-carboxamide

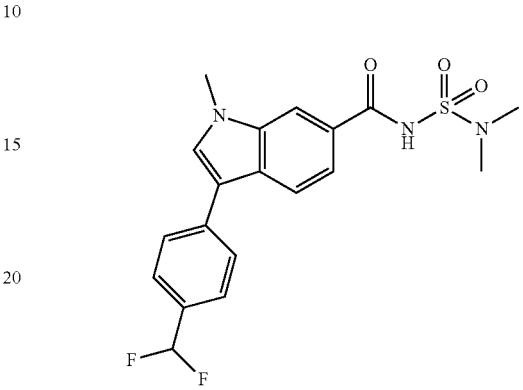

Prepared as in Example 30 using sulfonamide of dimethylsulfamic acid and intermediate acid from Example 30. Obtained 10.2 mg, 67% yield. $^1$H NMR (500 MHz, DMSO-d6) δ 11.73 (s, 1H), 8.31 (s, 1H), 8.08 (s, 1H), 8.01 (d, J=8.5 Hz, 1H), 7.84 (d, J=8.2 Hz, 2H), 7.76 (dd, J=8.5, 1.2 Hz, 1H), 7.65 (d, J=7.9 Hz, 2H), 7.07 (t, J=56.0 Hz, 1H), 3.95 (s, 3H), 2.92 (s, 6H); $^{19}$F NMR (471 MHz, DMSO-d6) δ −108.65 (s, 2F); LCMS (ESI) m/e 408.0 [(M+H)+, calcd $C_{19}H_{20}F_2N_3O_3S_1$, 408.1]; LC/MS retention time (method D): $t_R$=1.89 min.

EXAMPLE 33

3-(4-(Difluoromethyl)phenyl)-N—(N,N-dimethylsulfamoyl)-1-methyl-1H-indole-6-carboxamide

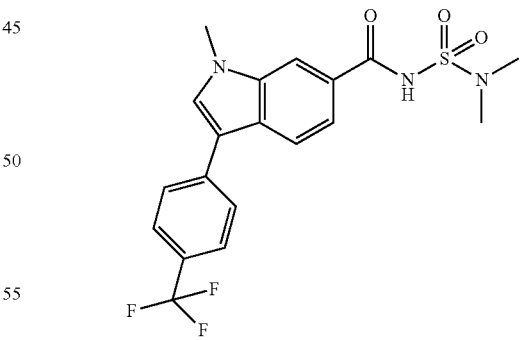

Prepared as in Example 18 using sulfonamide of dimethylsulfamic acid and intermediate acid from Example 18, Part B. Obtained 9.8 mg, 74% yield. $^1$H NMR (500 MHz, DMSO-d6) δ 11.66 (br. s., 1H), 8.27 (s, 1H), 8.04 (s, 1H), 8.01 (d, J=8.5 Hz, 1H), 7.90 (d, J=8.2 Hz, 2H), 7.75 (d, J=8.2 Hz, 3H), 3.94 (s, 3H), 2.92 (s, 6H); $^{19}$F NMR (471 MHz, DMSO-d6) δ-61.25 (s, 3F); LCMS (ESI) m/e 426.0 [(M+H)+, calcd $C_{19}H_{19}F_3N_3O_3S_1$, 426.1]; LC/MS retention time (method D): $t_R$=2.09 min.

EXAMPLE 34

3-(5-Chloro-6-(cyclopropylmethoxy)pyridin-3-yl)-1-methyl-N-(methylsulfonyl)-1H-indole-6-carboxamide

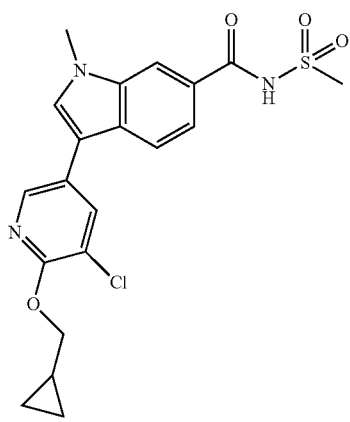 [SMILES: Cn1cc(-c2cnc(OCC3CC3)c(Cl)c2)c2ccc(C(=O)NS(C)(=O)=O)cc21]

Part A:
5-Bromo-3-chloro-2-(cyclopropylmethoxy)pyridine

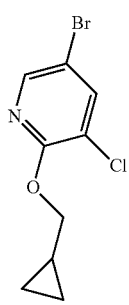 [SMILES: Clc1cc(Br)cnc1OCC1CC1]

Prepared as in Example 23. Obtained 4.1 g, 90% yield. $^1$H NMR (400 MHz, CHLOROFORM-d) δ 8.08 (d, J=2.2 Hz, 1H), 7.77 (d, J=2.2 Hz, 1H), 4.23 (d, J=7.1 Hz, 2H), 1.40-1.27 (m, 1H), 0.67-0.60 (m, 2H), 0.43-0.37 (m, 2H); LCMS (ESI) m/e 261.8 [(M+H)$^+$, calcd C$_9$H$_{10}$Br$_1$Cl$_1$N$_1$O$_1$, 262.0]; LC/MS retention time (method A): t$_R$=2.07 min.

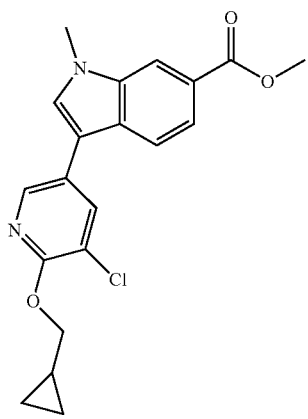 [SMILES: COC(=O)c1ccc2c(-c3cnc(OCC4CC4)c(Cl)c3)cn(C)c2c1]

Part B: Methyl 3-(5-chloro-6-(cyclopropylmethoxy)pyridin-3-yl)-1-methyl-1H-indole-6-carboxylate Prepared as in Example 2 part B. Obtained 0.159 g, 36% yield. $^1$H NMR (400 MHz, CHLOROFORM-d) δ 8.29 (d, J=2.0 Hz, 1H), 8.15 (d, J=0.8 Hz, 1H), 7.90-7.79 (m, 3H), 7.33 (s, 1H), 4.29 (d, J=7.0 Hz, 2H), 3.98 (s, 3H), 3.91 (s, 3H), 1.45-1.34 (m, 1H), 0.69-0.62 (m, 2H), 0.46-0.40 (m, 2H); LCMS (ESI) m/e 371.2 [(M+H)$^+$, calcd C$_{20}$H$_{20}$Cl$_1$N$_2$O$_3$, 371.1]; LC/MS retention time (method A): t$_R$=2.13 min.

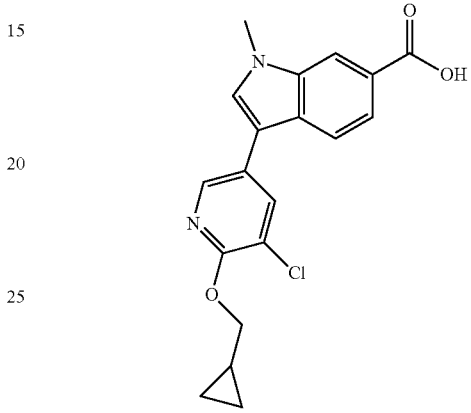

Part C: 3-(5-Chloro-6-(cyclopropylmethoxy)pyridin-3-yl)-1-methyl-1H-indole-6-carboxylic Acid Prepared as in Example 18, Part B. Obtained 0.151 g, 99% yield. LCMS (ESI) m/e 357.1 [(M+H)$^+$, calcd C$_{19}$H$_{18}$Cl$_1$N$_2$O$_3$, 357.1]; LC/MS retention time (method D): t$_R$=2.27 min.

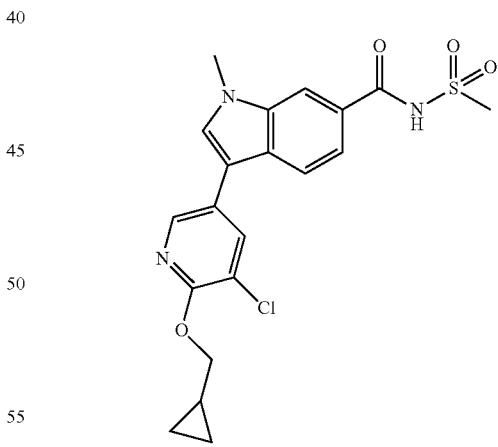

Part D: 3-(5-Chloro-6-(cyclopropylmethoxy)pyridin-3-yl)-1-methyl-N-(methylsulfonyl)-1H-indole-6-carboxamide Prepared as in Example 2, Part D using methanesulfonamide. Obtained 20.7 mg, 75% yield. $^1$H NMR (500 MHz, DMSO-d6) δ 8.43 (d, J=1.8 Hz, 1H), 8.28 (s, 1H), 8.12 (d, J=1.8 Hz, 1H), 7.99 (s, 1H), 7.91 (d, J=8.5 Hz, 1H), 7.77 (d, J=8.2 Hz, 1H), 4.28 (d, J=7.0 Hz, 2H), 3.94 (s, 3H), 3.37 (s, 3H), 1.37-1.27 (m, 1H), 0.63-0.57 (m, 2H), 0.43-0.38 (m, 2H); LCMS (ESI) m/e 434.0 [(M+H)⁺, calcd C$_{20}$H$_{21}$Cl$_1$N$_3$O$_4$S$_1$, 434.1]; LC/MS retention time (method D): t$_R$=2.26 min.

EXAMPLE 35

3-(5-Chloro-6-(cyclopropylmethoxy)pyridin-3-yl)-N-(cyclopropylsulfonyl)-1-methyl-1H-indole-6-carboxamide

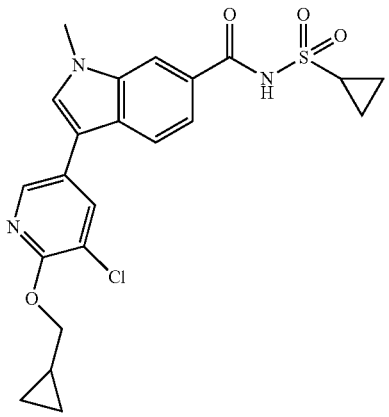 [SMILES: Cn1cc(-c2cnc(OCC3CC3)c(Cl)c2)c2ccc(C(=O)NS(=O)(=O)C3CC3)cc21]

Prepared as in Example 18. Obtained 13.4 mg, 60% yield. ¹H NMR (500 MHz, DMSO-d6) δ 8.43 (d, J=2.1 Hz, 1H), 8.27 (s, 1H), 8.12 (d, J=1.8 Hz, 1H), 7.99 (s, 1H), 7.91 (d, J=8.5 Hz, 1H), 7.76 (d, J=8.5 Hz, 1H), 4.28 (d, J=7.0 Hz, 2H), 3.94 (s, 3H), 1.38-1.28 (m, 1H), 1.23-1.18 (m, 2H), 1.15-1.09 (m, 2H), 0.63-0.58 (m, 2H), 0.40 (q, J=4.8 Hz, 2H) Note: 1H buried under DMSO peak; LCMS (ESI) m/e 460.0 [(M+H)⁺, calcd C$_{22}$H$_{23}$C$_{11}$N$_3$O$_4$S$_1$, 460.1]; LC/MS retention time (method D): t$_R$=2.30 min.

EXAMPLE 36

3-(5-Chloro-6-isobutoxypyridin-3-yl)-N-(ethylsulfonyl)-1-methyl-1H-indole-6-carboxamide

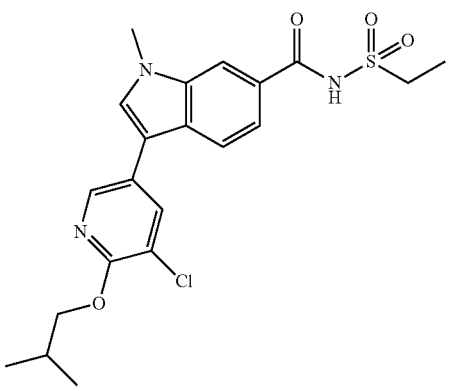 [SMILES: CCS(=O)(=O)NC(=O)c1ccc2c(-c3cnc(OCC(C)C)c(Cl)c3)cn(C)c2c1]

Prepared as in Example 2 using intermediate 3-(5-chloro-6-isobutoxypyridin-3-yl)-1-methyl-1H-indole-6-carboxylic acid and ethanesulfonamide. Obtained 7.6 mg, 46% yield. ¹H NMR (500 MHz, DMSO-d6) δ 8.44 (d, J=1.8 Hz, 1H), 8.29 (s, 1H), 8.12 (d, J=1.8 Hz, 1H), 7.98 (s, 1H), 7.90 (d, J=8.9 Hz, 1H), 7.78-7.75 (m, 1H), 4.21 (d, J=6.4 Hz, 2H), 3.94 (s, 3H), 3.51 (q, J=7.4 Hz, 2H), 2.12 (dt, J=13.4, 6.7 Hz, 1H), 1.30 (t, J=7.3 Hz, 3H), 1.03 (d, J=6.7 Hz, 6H); LCMS (ESI) m/e 450.0 [(M+H)⁺, calcd C$_{21}$H$_{25}$Cl$_1$N$_3$O$_4$S$_1$, 450.1]; LC/MS retention time (method D): t$_R$=2.37 min.

EXAMPLE 37

3-(5-Chloro-6-isobutoxypyridin-3-yl)-N-(isopropylsulfonyl)-1-methyl-1H-indole-6-carboxamide

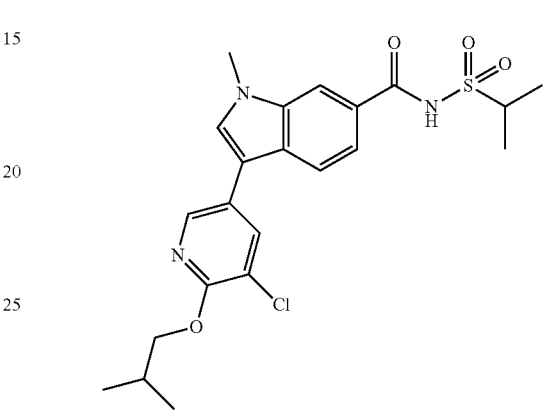

Prepared as in Example 2 using intermediate 3-(5-chloro-6-isobutoxypyridin-3-yl)-1-methyl-1H-indole-6-carboxylic acid and propane-2-sulfonamide. Obtained 13.7 mg, 85% yield. ¹H NMR (500 MHz, DMSO-d6) δ 8.43 (d, J=2.1 Hz, 1H), 8.28 (s, 1H), 8.12 (d, J=2.1 Hz, 1H), 7.99 (s, 1H), 7.90 (d, J=8.5 Hz, 1H), 7.78-7.74 (m, 1H), 4.21 (d, J=6.7 Hz, 2H), 3.94 (s, 3H), 3.89 (dt, J=13.7, 6.8 Hz, 1H), 2.12 (dt, J=13.4, 6.6 Hz, 1H), 1.36 (d, J=6.7 Hz, 6H), 1.03 (d, J=6.7 Hz, 6H); LCMS (ESI) m/e 464.0 [(M+H)⁺, calcd C$_{22}$H$_{27}$C$_{11}$N$_3$O$_4$S$_1$, 464.1]; LC/MS retention time (method D): t$_R$=1.99 min.

EXAMPLE 38

N-(tert-butylsulfonyl)-3-(5-chloro-6-isobutoxypyridin-3-yl)-1-methyl-1H-indole-6-carboxamide

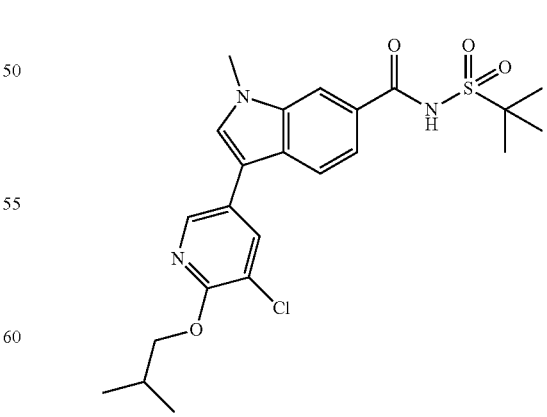

Prepared as in Example 2 using intermediate 3-(5-chloro-6-isobutoxypyridin-3-yl)-1-methyl-1H-indole-6-carboxylic acid and 2-methylpropane-2-sulfonamide. Obtained 11.9 mg, 70% yield. $^1$H NMR (500 MHz, DMSO-d6) δ 8.44 (d, J=1.8 Hz, 1H), 8.23 (s, 1H), 8.12 (d, J=1.8 Hz, 1H), 7.97 (s, 1H), 7.89 (d, J=8.5 Hz, 1H), 7.74 (d, J=8.2 Hz, 1H), 4.21 (d, J=6.4 Hz, 2H), 3.94 (s, 3H), 2.12 (dt, J=13.2, 6.7 Hz, 1H), 1.46 (s, 9H), 1.04 (d, J=6.7 Hz, 6H); LCMS (ESI) m/e 478.0 [(M+H)$^+$, calcd C$_{23}$H$_{29}$C$_{l1}$N$_3$O$_4$S$_1$, 478.1]; LC/MS retention time (method D): $t_R$=2.46 min.

EXAMPLE 39

3-(5-Chloro-6-isobutoxypyridin-3-yl)-1-methyl-N-(methylsulfonyl)-1H-indazole-6-carboxamide

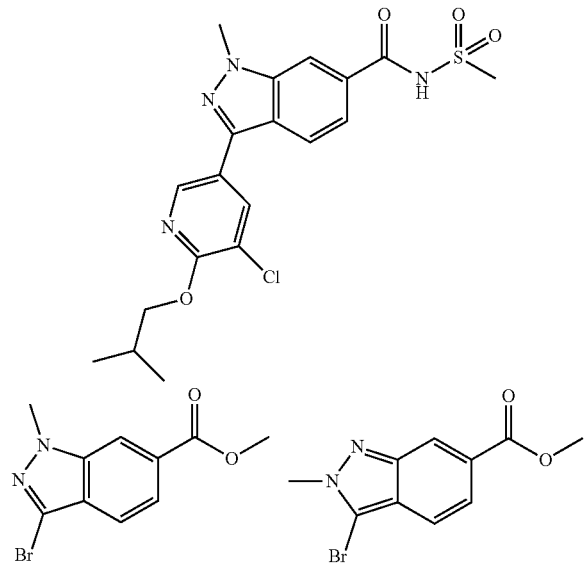

Part A: Methyl 3-bromo-1-methyl-1H-indazole-6-carboxylate and Methyl 3-bromo-2-methyl-2H-indazole-6-carboxylate Sodium hydride (0.152 g, 3.79 mmol) was added to a solution of methyl 3-bromo-1H-indazole-6-carboxylate (0.6451 g, 2.53 mmol) in THF (10 mL) at 0° C. The reaction was stirred for 10 min then methyl iodide (0.237 mL, 3.79 mmol) was added to the reaction mixture. The reaction was stirred overnight while it warmed up to room temperature. The solvent was removed under vacuum and the crude residue was partitioned between water and ethyl acetate. The aqueous layer was separated and extracted two more times with ethyl acetate. The ethyl acetate layers were combined, dried (Na2SO4), filtered and concentrated to give the crude product as a mixture of N1-methyl and N2-methyl indazoles. The residue was purified via silica gel flash column chromatography eluting with ethyl acetate in hexane from 0 to 25%. The N1-methyl and N2-methyl indazole isomers were determined by an NOE experiment.

N$_1$ Methyl: Obtained methyl 3-bromo-1-methyl-1H-indazole-6-carboxylate 0.228 g, 34% yield. $^1$H NMR (500 MHz, CHLOROFORM-d) δ 8.14 (d, J=0.8 Hz, 1H), 7.87-7.83 (m, 1H), 7.64 (dd, J=8.5, 0.8 Hz, 1H), 4.12 (s, 3H), 3.99 (s, 3H); LCMS (ESI) me 269.0 [(M+H)$^+$, calcd C$_{10}$H$_{10}$Br$_1$N$_2$O$_2$, 269.0]; LC/MS retention time (method D): $t_R$=1.74 min.

N$_2$ Methyl: Obtained methyl 3-bromo-2-methyl-2H-indazole-6-carboxylate 0.121 g, 18% yield. $^1$H NMR (500 MHz, CHLOROFORM-d) δ 8.46 (s, 1H), 7.76 (dd, J=8.9, 1.2 Hz, 1H), 7.55 (dd, J=8.9, 0.8 Hz, 1H), 4.25 (s, 3H), 3.98 (s, 3H); LCMS (ESI) me 268.9 [(M+H)$^+$, calcd C$_{10}$H$_{10}$Br$_1$N$_2$O$_2$, 269.0]; LC/MS retention time (method D): $t_R$=1.62 min.

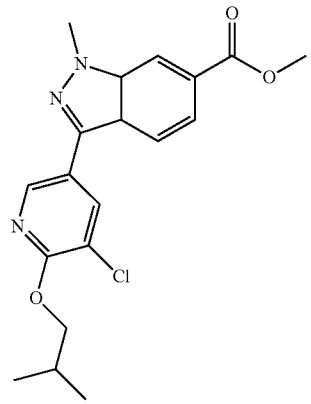 [SMILES: COC(=O)C1=CC2C(C=C1)C(c1cnc(OCC(C)C)c(Cl)c1)=NN2C]

Part B: Methyl 3-(5-chloro-6-isobutoxypyridin-3-yl)-1-methyl-3a,7a-dihydro-1H-indazole-6-carboxylate A mixture of sodium carbonate (0.086 mL, 0.172 mmol), PdCl2(dppf) (5.23 mg, 7.15 μmol), 3-chloro-2-isobutoxy-5-(4,4,5,5-tetramethyl-1,3,2-dioxaborolan-2-yl)pyridine (0.045 g, 0.143 mmol) and methyl 3-bromo-1-methyl-1H-indazole-6-carboxylate (0.0385 g, 0.143 mmol) in 1,4-dioxane (0.7 mL) was heated at 80° C. for 10 hours. The reaction was diluted with ethyl acetate and dried with Na$_2$SO$_4$. The mixture was filtered and concentrated. The residue was purified via silica gel flash column chromatography eluting with ethyl acetate in hexane from 0 to 50% to give the desired product combined with some remaining starting material (0.036 g, 55% pure, 37% yield of product). This mixture was used as is. LCMS (ESI) m/e 374.1 [(M+H)$^+$, calcd C$_{19}$H$_{21}$Cl$_1$N$_3$O$_3$, 374.1]; LC/MS retention time (method A): $t_R$=2.32 min.

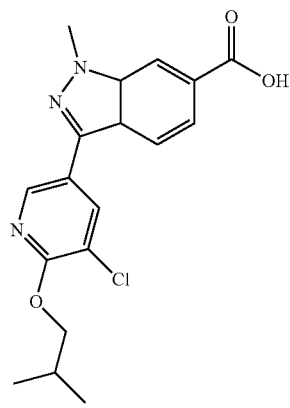 [SMILES: CC(C)COc1ncc(C2=NN(C)C3C=C(C(=O)O)C=CC23)cc1Cl]

Part C: 3-(5-Chloro-6-isobutoxypyridin-3-yl)-1-methyl-3a,7a-dihydro-1H-indazole-6-carboxylic Acid A mixture of LiOH (24.0 mg, 1.002 mmol) and methyl 3-(5-chloro-6-isobutoxypyridin-3-yl)-1-methyl-1H-indazole-6-carboxylate (0.0364 g, 0.097 mmol) in THF (1.5 mL), water (0.5 mL) and MeOH (0.5 mL) was stirred at room temperature overnight. LCMS showed incomplete conversion of the starting material. The reaction was continued to stir at room temperature for 24 hours. The volatiles were removed under vacuum. 1N HCl (2.2 mL) was added to the residue and the solution was extracted with ethyl acetate two times. The ethyl acetate layers were combined, dried with Na$_2$SO$_4$, filtered and concentrated to give the crude product as an off white solid (33.5 mg, 51% purity, 49% yield). This mixture was used as is. LCMS (ESI) m/e 358.1 [(M−H)$^+$, calcd C$_{18}$H$_{17}$C$_{11}$N$_3$O$_3$, 358.1]; LC/MS retention time (method A): t$_R$=1.54 min.

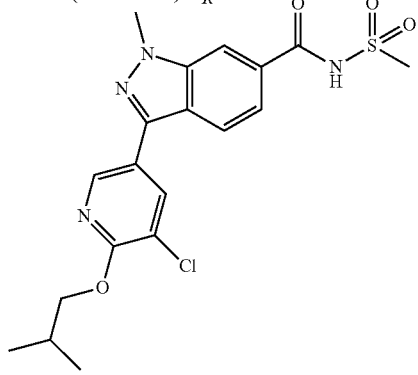 [SMILES: CC(C)COc1ncc(-c2nn(C)c3cc(C(=O)NS(C)(=O)=O)ccc23)cc1Cl]

Part D: 3-(5-Chloro-6-isobutoxypyridin-3-yl)-1-methyl-N-(methylsulfonyl)-1H-indazole-6-carboxamide Prepared as in Example 2 using intermediate 3-(5-Chloro-6-isobutoxypyridin-3-yl)-1-methyl-3a,7a-dihydro-1H-indazole-6-carboxylic acid and mathanesulfonamide. Obtained 6.9 mg, 15% yield. $^1$H NMR (500 MHz, DMSO-d6) δ 8.72 (d, J=2.1 Hz, 1H), 8.41 (s, 1H), 8.35 (d, J=1.8 Hz, 1H), 8.18 (d, J=8.5 Hz, 1H), 7.80-7.76 (m, 1H), 4.25 (d, J=6.7 Hz, 2H), 4.20 (s, 3H), 3.38 (s, 3H), 2.14 (dt, J=13.2, 6.7 Hz, 1H), 1.04 (d, J=6.7 Hz, 6H); LCMS (ESI) m/e 437.0 [(M+H)$^+$, calcd C$_{19}$H$_{22}$Cl$_1$N$_4$O$_4$S$_1$, 437.1]; LC/MS retention time (method D): t$_R$=1.79 min.

EXAMPLE 40

3-(5-Chloro-6-isobutoxypyridin-3-yl)-2-methyl-N-(methylsulfonyl)-2H-indazole-6-carboxamide

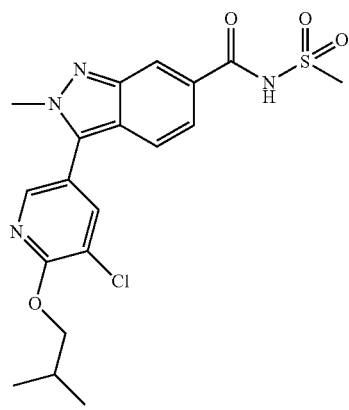 [SMILES: CC(C)COc1ncc(-c2c3ccc(C(=O)NS(C)(=O)=O)cc3nn2C)cc1Cl]

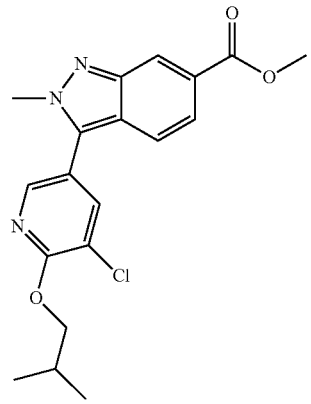

Part A: Methyl 3-(5-chloro-6-isobutoxypyridin-3-yl)-2-methyl-2H-indazole-6-carboxylate A mixture of sodium carbonate (0.044 mL, 0.088 mmol), PdCl2(dppf) (2.68 mg, 3.66 μmol),3-chloro-2-isobutoxy-5-(4,4,5,5-tetramethyl-1,3,2-dioxaborolan-2-yl)pyridine (0.023 g, 0.073 mmol) and methyl 3-bromo-2-methyl-2H-indazole-6-carboxylate obtained in Example 39, Part A (0.0197 g, 0.073 mmol) in 1,4-dioxane (0.5 mL) was heated at 80° C. for 10 hours. The reaction was diluted with ethyl acetate and dried with Na2SO4. The mixture was filtered and concentrated. The residue was purified via silica gel flash column chromatography eluting with ethyl acetate in hexane from 0 to 50% to give the desired product (0.017 g, 62% yield). $^1$H NMR (400 MHz, CHLOROFORM-d) δ 8.51 (t, J=1.0 Hz, 1H), 8.21 (d, J=2.3 Hz, 1H), 7.81 (d, J=2.0 Hz, 1H), 7.74 (dd, J=8.8, 1.3 Hz, 1H), 7.56 (dd, J=8.9, 0.9 Hz, 1H), 4.26 (d, J=6.5 Hz, 2H), 4.22 (s, 3H), 3.97 (s, 3H), 2.22 (dt, J=13.4, 6.7 Hz, 1H), 1.10 (d, J=6.8 Hz, 6H); LCMS (ESI) m/e 374.1 [(M+H)$^+$, calcd C$_{19}$H$_{21}$C$_{11}$N$_3$O$_3$, 374.1]; LC/MS retention time (method A): t$_R$=2.15 min.

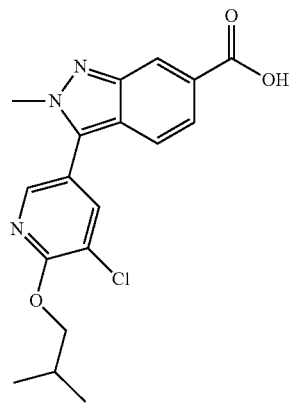 [SMILES: CC(C)COc1ncc(-c2c3ccc(C(=O)O)cc3nn2C)cc1Cl]

Part B: 3-(5-chloro-6-isobutoxypyridin-3-yl)-2-methyl-2H-indazole-6-carboxylic Acid Prepared as described in Example 39, Part C to obtain title compound 16 mg, 99% yield. LCMS (ESI) m/e 360.1 [(M−H)$^+$, calcd C$_{18}$H$_{19}$Cl$_1$N$_3$O$_3$, 360.1]; LC/MS retention time (method A): t$_R$=1.47 min.

Part C: 3-(5-Chloro-6-isobutoxypyridin-3-yl)-2-methyl-N-(methylsulfonyl)-2H-indazole-6-carboxamide

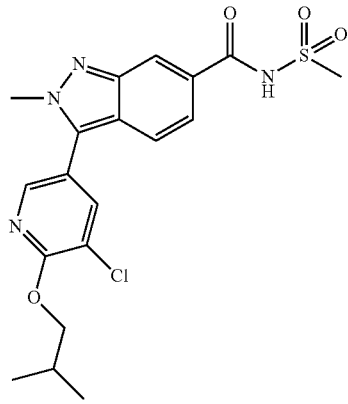

Prepared as described in Example 39, Part D using intermediate 3-(5-chloro-6-isobutoxypyridin-3-yl)-2-methyl-2H-indazole-6-carboxylic acid and mathanesulfonamide. Obtained 4.2 mg, 45% yield. $^1$H NMR (500 MHz, DMSO-d6) δ 8.40 (d, J=2.1 Hz, 1H), 8.34 (s, 1H), 8.24 (d, J=2.1 Hz, 1H), 7.67-7.59 (m, 2H), 4.27 (d, J=6.4 Hz, 2H), 4.19 (s, 3H), 3.21 (s, 3H), 2.15 (dt, J=13.6, 6.6 Hz, 1H), 1.05 (d, J=6.7 Hz, 6H); LCMS (ESI) m/e 437.0 [(M+H)$^+$, calcd $C_{19}H_{22}Cl_1N_4O_4S_1$, 437.1]; LC/MS retention time (method D): $t_R$=2.08 min.

EXAMPLE 41

3-(5-Chloro-6-isobutoxypyridin-3-yl)-N-(cyclopropylsulfonyl)-2-methyl-2H-indazole-6-carboxamide

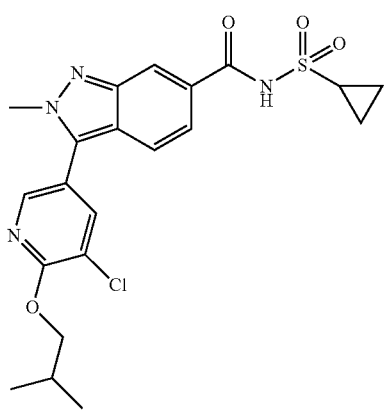 [SMILES: CC(C)COc1ncc(-c2c3ccc(C(=O)NS(=O)(=O)C4CC4)cc3nn2C)cc1Cl]

Prepared as described in Example 40 using intermediate 3-(5-chloro-6-isobutoxypyridin-3-yl)-2-methyl-2H-indazole-6-carboxylic acid and cyclopropanesulfonamide. Obtained 8.6 mg, 55% yield. $^1$H NMR (500 MHz, DMSO-d6) δ 8.41 (d, J=1.8 Hz, 1H), 8.35 (s, 1H), 8.24 (d, J=2.1 Hz, 1H), 7.65-7.62 (m, 2H), 4.28 (d, J=6.7 Hz, 2H), 4.20 (s, 3H), 3.12 (dt, J=8.4, 4.0 Hz, 1H), 2.16 (dt, J=13.3, 6.5 Hz, 1H), 1.16-1.12 (m, 2H), 1.07-1.02 (m, 8H); LCMS (ESI) m/e 463.0 [(M+H)$^+$, calcd $C_{21}H_{24}Cl_1N_4O_4S_1$, 463.1]; LC/MS retention time (method D): $t_R$=2.19 min.

Intermediates used for compounds prepared by General Scheme IV:

INTERMEDIATE G

2-Fluoro-4-methyl-5-nitrobenzoic Acid

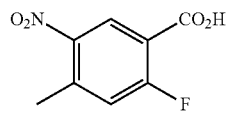

In a 250 mL round-bottomed flask was dissolved 2-fluoro-4-methylbenzoic acid (4 g, 26.0 mmol) in concentrated sulfuric acid (40 mL) at 0° C. (completely dissolved). A mixture of 12 N H2SO4 (1.69 mL, 31.1 mmol) and 70% nitric acid (2.485 mL, 38.9 mmol) was added dropwise. After stirring for 3 h at 0° C., an excess of ice water was added. The resulting solid was collected by vacuum filtration and dried to obtain the desired product (5.20 g, 100%) as a white solid. LCMS (ESI) m/e 200.4 [(M+H)$^+$, calcd $C_8H_7FNO_4$, 200.04]; LC/MS retention time (method A): $t_R$=0.72 min.

INTERMEDIATE H

Methyl 2-fluoro-4-methyl-5-nitrobenzoate

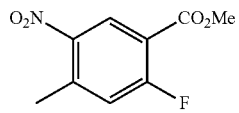

To a 500 mL round-bottomed flask was added 2-fluoro-4-methyl-5-nitrobenzoic acid (5.18 g, 26 mmol) in MeOH (40 mL) to give a colorless solution. H2SO4 (7.07 mL, 130 mmol) was slowly added. The reaction was heated to 65° C. overnight for 20 h. The mixture was concentrated and diluted with ice and water. The solid was collected by vacuum filtration and rinsed several times with cold water, then air-dried overnight to afford the desired product (5.12 g, 92%) as a white solid. LCMS (ESI) me 212.1 [(M–H)$^-$, calcd $C_9H_7FNO_4$, 212.04]; LC/MS retention time (method A): $t_R$=1.59 min.

INTERMEDIATE I

Methyl 4-(2-(dimethylamino)vinyl)-2-fluoro-5-nitrobenzoate

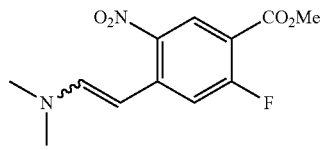 [SMILES: COC(=O)c1cc([N+](=O)[O-])c(C=CN(C)C)cc1F]

In a 250 mL round-bottomed flask was methyl 2-fluoro-4-methyl-5-nitrobenzoate (2.57 g, 12.06 mmol) in DMF (10 mL) to give a colorless solution. 1,1-dimethoxy-N,N-dimethylmethanamine (1.937 mL, 14.47 mmol) was added. The mixture was stirred under nitrogen at 100° C. for 1 h. LCMS showed two peaks.

After heating for another hours, the mixture was diluted with water. The solids were filtered and dried to obtain the desired product (2.77 g, 86%) as a mixture of E- and Z-isomers as a red solid. The material was used as is. LCMS (ESI) m/e 269.0 [(M+H)$^+$, calcd $C_{12}H_{14}FN_2O_4$, 269.09]; LC/MS retention time (method A): $t_R$=1.56 and 1.68 min.

INTERMEDIATE J

Methyl 5-fluoro-1H-indole-6-carboxylate

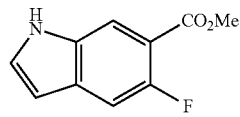 [SMILES: COC(=O)c1cc2[nH]ccc2cc1F]

In a 500 mL round-bottomed flask was added methyl 4-(2-(dimethylamino)vinyl)-2-fluoro-5-nitrobenzoate (2.77 g, 10.33 mmol) in ethyl acetate (100 mL) to give a red solution. Pd/C (0.110 g, 0.103 mmol) was added. After evacuating and refilling with H2, the mixture was stirred under hydrogen (balloon) for 2 h (deep red color faded). After evacuating and refilling with nitrogen, the mixture was filtered and rinsed with EtOAc. The combined organic solution was concentrated. The residue was purified by silica gel flash column chromatography up to 50% EtOAc/hexane to afford the desired product (1.40 g, 70%) as a yellow solid. The material was used as is. LCMS (ESI) m/e 192.1 [(M−H)$^-$, calcd $C_{10}H_9FNO_2$, 192.05]; LC/MS retention time (method A): $t_R$=1.41 min.

INTERMEDIATE K

Methyl 5-fluoro-3-iodo-1-methyl-1H-indole-6-carboxylate

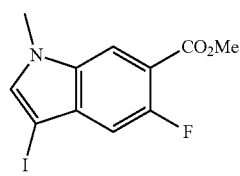 [SMILES: COC(=O)c1cc2c(cc1F)c(I)cn2C]

A mixture of KOH (0.651 g, 11.60 mmol) and methyl 5-fluoro-1H-indole-6-carboxylate (0.896 g, 4.64 mmol) in DMF (10 mL) was stirred at room temperature for 30 min. Iodine (1.177 g, 4.64 mmol) in DMF (5 mL) was added to the reaction mixture at room temperature. The reaction was stirred overnight for 16 h. LCMS showed the desired product to be the major peak (LCMS (ESI) m/e 318.0.1 [(M−H)$^-$, calcd $C_{10}H_6FINO_2$, 317.94]; LC/MS retention time (method A): $t_R$=1.67 min). MeI (0.348 mL, 5.57 mmol) was then added and the reaction mixture was stirred at rt for 5 h. LCMS showed the desired product (M+H=334.0, tR=1.79 min, Method A). Excess water was added and the solids were filtered and further rinsed with water. The solids were further dried overnight to afford the desired product (1.32 g, 85%) as a yellow solid: $^1$H NMR (400 MHz, Chloroform-d) δ 7.98 (d, J=5.7 Hz, 1H), 7.32 (s, 1H), 7.18 (d, J=11.3 Hz, 1H), 3.99 (s, 3H), 3.88 (s, 3H); $^{19}$F NMR (376 MHz, Chloroform-d) δ-121.09; LCMS (ESI) m/e 334.0 [(M+H)$^+$, calcd $C_{11}H_{10}FINO_2$, 333.97]; LC/MS retention time (method A): $t_R$=1.79 min.

INTERMEDIATE L

Methyl 3-(5-chloro-6-isobutoxypyridin-3-yl)-5-fluoro-1-methyl-1H-indole-6-carboxylate

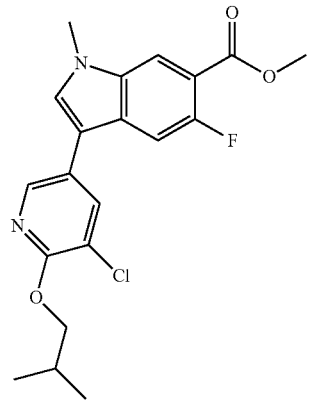 [SMILES: COC(=O)c1cc2c(cc1F)c(-c1cnc(OCC(C)C)c(Cl)c1)cn2C]

The compound was prepared following previously described procedures with formation of the boronate from the iodide. $^1$H NMR (400 MHz, Chloroform-d) δ 8.24 (d, J=2.1 Hz, 1H), 8.01 (d, J=5.8 Hz, 1H), 7.82 (d, J=2.2 Hz, 1H), 7.49 (d, J=11.8 Hz, 1H), 7.36 (s, 1H), 4.21 (d, J=6.7 Hz, 2H), 3.99 (s, 3H), 3.90 (s, 3H), 2.20 (hept, J=6.7 Hz, 1H), 1.09 (d, J=6.7 Hz, 6H); $^{19}$F NMR (376 MHz, Chloroform-d) δ-121.23; LCMS (ESI) m/e 391.0 [(M+H)$^+$, calcd $C_{20}H_{21}Cl_1FlN_2O_3$, 391.12]; LC/MS retention time (method D): $t_R$=1.19 min.

INTERMEDIATE M

Methyl 5-fluoro-3-(6-isobutoxypyridin-3-yl)-1-methyl-1H-indole-6-carboxylate

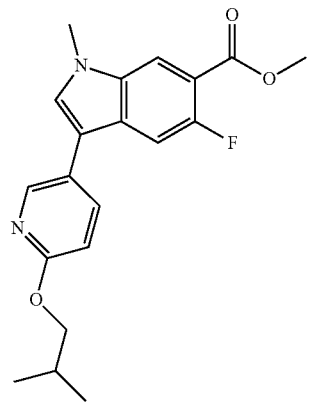 [SMILES: COC(=O)c1cc2c(cc1F)c(-c1ccc(OCC(C)C)nc1)cn2C]

The compound was prepared following previously described procedures with formation of the boronate from the iodide. $^1$H NMR (400 MHz, Chloroform-d) δ 8.39-8.34 (m, 1H), 8.01 (d, J=5.8 Hz, 1H), 7.77 (dd, J=8.6, 2.5 Hz, 1H), 7.50 (d, J=12.0 Hz, 1H), 7.35 (s, 1H), 6.85 (dd, J=8.5, 0.7 Hz, 1H), 4.13 (d, J=6.7 Hz, 2H), 3.99 (s, 3H), 3.90 (s, 3H), 2.15 (hept, J=6.7 Hz, 1H), 1.07 (d, J=6.7 Hz, 6H); $^{19}$F NMR (376 MHz, Chloroform-d) δ -121.69; LCMS (ESI) m/e 357.2 [(M+H)$^+$, calcd $C_{20}H_{22}F_1N_2O_3$, 357.2]; LC/MS retention time (method D): $t_R$=2.18 min.

INTERMEDIATE N

Methyl 5-fluoro-1-methyl-3-(4-(trifluoromethyl)phenyl)-1H-indole-6-carboxylate

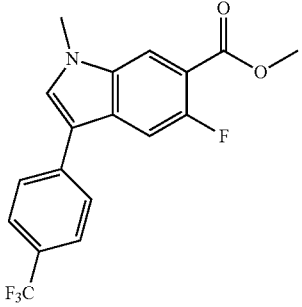 [SMILES: COC(=O)c1cc2c(cc1F)c(-c1ccc(C(F)(F)F)cc1)cn2C]

The compound was prepared following previously described procedures with formation of the boronate from the iodide. $^1$H NMR (400 MHz, Chloroform-d) δ 8.04 (d, J=5.8 Hz, 1H), 7.71 (s, 4H), 7.61 (d, J=12.0 Hz, 1H), 7.49 (s, 1H), 4.01 (s, 3H), 3.93 (s, 3H); $^{19}$F NMR (376 MHz, Chloroform-d) δ -62.35, -121.02; LCMS (ESI) m/e 351.9 [(M+H)$^+$, calcd $C_{18}H_{14}F_4NO_3$, 352.10]; LC/MS retention time (method D): $t_R$=1.08 min.

INTERMEDIATE O

Methyl 3-(4-(difluoromethyl)phenyl)-5-fluoro-1-methyl-1H-indole-6-carboxylate

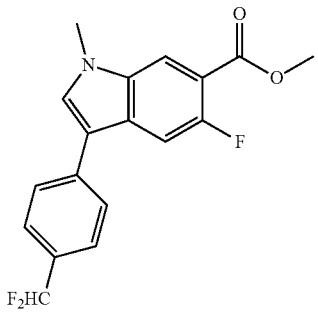 [SMILES: COC(=O)c1cc2c(cc1F)c(-c1ccc(C(F)F)cc1)cn2C]

The compound was prepared following previously described procedures with formation of the boronate from the iodide. $^1$H NMR (400 MHz, Chloroform-d) δ 8.04 (d, J=5.8 Hz, 1H), 7.71 (s, 4H), 7.61 (d, J=12.0 Hz, 1H), 7.49 (s, 1H), 4.01 (s, 3H), 3.93 (s, 3H); $^{19}$F NMR (376 MHz, Chloroform-d) δ -62.35, -121.02; LCMS (ESI) m/e 334.2 [(M+H)$^+$, calcd $C_{18}H_{15}F_3N_1O_2$, 334.1]; LC/MS retention time (method A): $t_R$=1.94 min.

INTERMEDIATE P 3-(5-Chloro-6-isobutoxypyridin-3-yl)-5-fluoro-1-methyl-1H-indole-6-carboxylic Acid

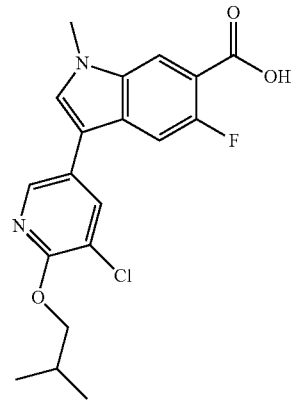 [SMILES: CC(C)COc1ncc(-c2cn(C)c3cc(C(=O)O)c(F)cc23)cc1Cl]

The compound was prepared following previously described procedure. LCMS (ESI) m/e 375.1 [(M-H)$^+$, calcd $C_{19}H_{19}Cl_1FlN_2O_3$, 375.1]; LC/MS retention time (method A): $t_R$=1.56 min.

INTERMEDIATE Q

5-Fluoro-3-(6-isobutoxypyridin-3-yl)-1-methyl-1H-indole-6-carboxylic Acid

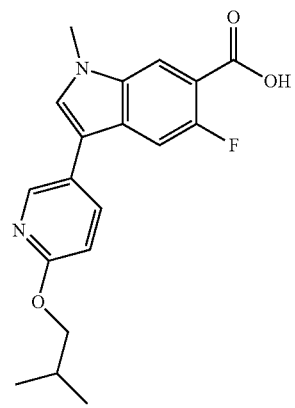 [SMILES: CC(C)COc1ccc(-c2cn(C)c3cc(C(=O)O)c(F)cc23)cn1]

The compound was prepared following previously described procedure. LCMS (ESI) m/e 343.1 [(M+H)$^+$, calcd $C_{19}H_{20}F_1N_2O_3$, 343.1]; LC/MS retention time (method A): $t_R$=1.44 min.

INTERMEDIATE R

5-Fluoro-1-methyl-3-(4-(trifluoromethyl)phenyl)-1H-indole-6-carboxylic Acid

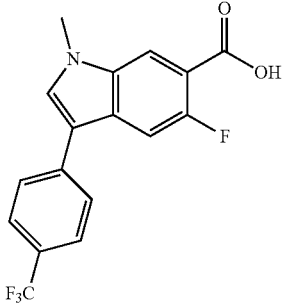 [SMILES: Cn1cc(-c2ccc(C(F)(F)F)cc2)c2cc(F)c(C(=O)O)cc21]

The compound was prepared following previously described procedure. LCMS (ESI) m/e 338.1 [(M+H)$^+$, calcd $C_{17}H_{12}F_4N_1O_2$, 338.1]; LC/MS retention time (method A): $t_R$=1.46 min.

INTERMEDIATE S 3-(4-(Difluoromethyl)phenyl)-5-fluoro-1-methyl-1H-indole-6-carboxylic Acid

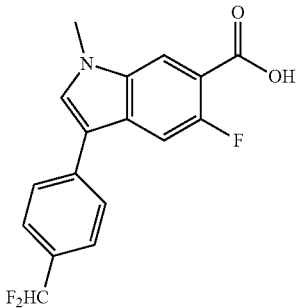 [SMILES: Cn1cc(-c2ccc(C(F)F)cc2)c2cc(F)c(C(=O)O)cc21]

The compound was prepared following previously described procedure. LCMS (ESI) m/e 319.2 [(M+H)$^+$, calcd $C_{17}H_{13}F_3N_{10}O_2$, 319.1]; LC/MS retention time (method A): $t_R$=1.36 min.

EXAMPLE 42

3-(5-Chloro-6-isobutoxypyridin-3-yl)-5-fluoro-1-methyl-N-(methylsulfonyl)-1H-indole-6-carboxamide

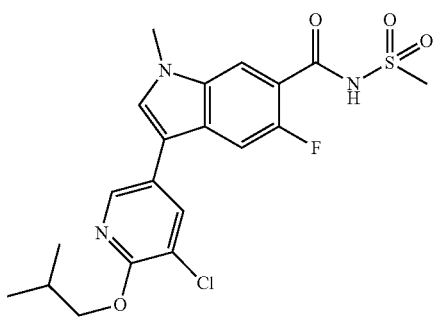 [SMILES: CC(C)COc1ncc(-c2cn(C)c3cc(C(=O)NS(C)(=O)=O)c(F)cc23)cc1Cl]

Prepared from intermediate P as described in Example 2, Part D. Obtained 10.7 mg, 74% yield. $^1$H (500 MHz, DMSO-d6) δ 8.40 (d, J=2.2 Hz, 1H), 8.13 (d, J=2.2 Hz, 1H), 7.97 (s, 1H), 7.88 (d, J=6.0 Hz, 1H), 7.60 (d, J=11.8 Hz, 1H), 4.17 (d, J=6.6 Hz, 2H), 3.89 (s, 3H), 2.55 (s, 3H), 2.10 (dt, J=13.5, 6.8 Hz, 1H), 1.01 (d, J=6.7 Hz, 6H); $^{19}$F NMR (471 MHz, DMSO-d6) δ-123.94; LCMS (ESI) m/e 452.2 [(M−H)$^+$, calcd $C_{20}H_{20}Cl_1F_1N_3O_4S_1$, 452.1]; LC/MS retention time (method A): $t_R$=1.60 min.

EXAMPLE 43

3-(5-Chloro-6-isobutoxypyridin-3-yl)-N-(cyclopropylsulfonyl)-5-fluoro-1-methyl-1H-indole-6-carboxamide

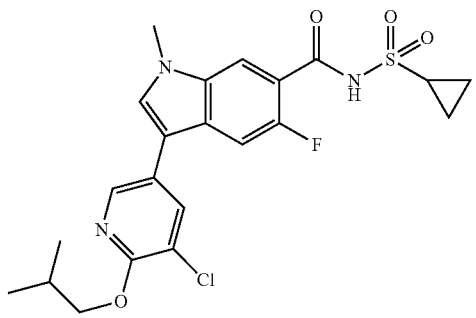 [SMILES: CC(C)COc1ncc(-c2cn(C)c3cc(C(=O)NS(=O)(=O)C4CC4)c(F)cc23)cc1Cl]

Prepared from intermediate P as described in Example 2, Part D. Obtained 8.8 mg, 59% yield. $^1$H NMR (500 MHz, DMSO-d6) δ 8.41 (d, J=2.2 Hz, 1H), 8.14 (d, J=2.2 Hz, 1H), 8.05 (s, 1H), 7.92 (d, J=5.9 Hz, 1H), 7.72 (d, J=11.9 Hz, 1H), 4.17 (d, J=6.6 Hz, 2H), 3.91 (s, 3H), 3.19-3.09 (m, 1H), 2.11 (dq, J=13.4, 6.7 Hz, 1H), 1.21-1.12 (m, 4H), 1.01 (d, J=6.7 Hz, 6H); $^{19}$F NMR (471 MHz, DMSO-d6) δ-124.04; LCMS (ESI) m/e 478.2 [(M−H)$^+$, calcd $C_{22}H_{22}Cl_1F_1N_3O_4S_1$, 478.1]; LC/MS retention time (method A): $t_R$=1.67 min.

EXAMPLE 44

5-Fluoro-3-(6-isobutoxypyridin-3-yl)-1-methyl-N-(methylsulfonyl)-1H-indole-6-carboxamide

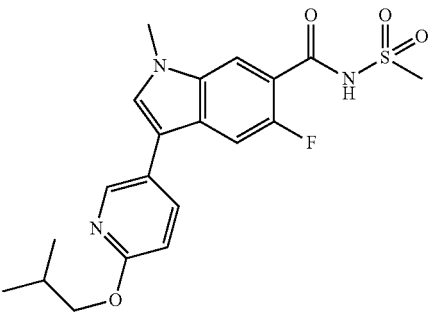 [SMILES: CC(C)COc1ccc(-c2cn(C)c3cc(C(=O)NS(C)(=O)=O)c(F)cc23)cn1]

Prepared from intermediate Q as described in Example 2, Part D. Obtained 7.9 mg, 49% yield. $^1$H NMR (500 MHz, DMSO-d6) δ 8.42 (d, J=2.7 Hz, 1H), 7.98 (dd, J=8.5, 2.5 Hz, 1H), 7.96 (s, 1H), 7.92 (d, J=5.9 Hz, 1H), 7.64 (d, J=11.9 Hz, 1H), 6.91 (d, J=8.5 Hz, 1H), 4.07 (d, J=6.6 Hz, 2H), 3.91 (s, 3H), 3.38 (s, 3H), 2.06 (dp, J=13.5, 6.8 Hz, 1H), 0.99 (d, J=6.7 Hz, 6H); $^{19}$F NMR (471 MHz, DMSO-d6) δ-124.53; LCMS (ESI) m/e 418.2 [(M–H)$^+$, calcd C$_{20}$H$_{21}$F$_1$N$_3$O$_4$S$_1$, 418.1]; LC/MS retention time (method A): t$_R$=1.47 min.

EXAMPLE 45

N-(Cyclopropylsulfonyl)-5-fluoro-3-(6-isobutoxy-pyridin-3-yl)-1-methyl-1H-indole-6-carboxamide

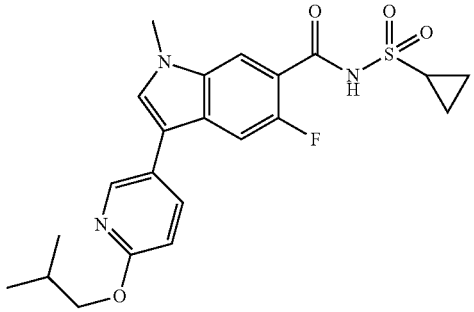 [SMILES: CC(C)COc1ccc(-c2cn(C)c3cc(C(=O)NS(=O)(=O)C4CC4)c(F)cc23)cn1]

Prepared from intermediate Q as described in Example 2, Part D. Obtained 7.9 mg, 57% yield. $^1$H NMR (500 MHz, DMSO-d6) δ 8.43 (d, J=2.5 Hz, 1H), 7.98 (dd, J=8.5, 2.5 Hz, 1H), 7.95 (s, 1H), 7.91 (d, J=6.0 Hz, 1H), 7.63 (d, J=11.9 Hz, 1H), 6.91 (d, J=8.6 Hz, 1H), 4.08 (d, J=6.7 Hz, 2H), 3.91 (s, 3H), 3.12 (ddd, J=12.8, 8.1, 4.8 Hz, 1H), 2.07 (dp, J=13.4, 6.8 Hz, 1H), 1.20-1.07 (m, 4H), 1.00 (d, J=6.7 Hz, 6H); $^{19}$F NMR (471 MHz, DMSO-d6) δ-124.27; LCMS (ESI) m/e 444.2 [(M–H)$^+$, calcd C$_{22}$H$_{23}$F$_1$N$_3$O$_4$S$_1$, 444.1]; LC/MS retention time (method A): t$_R$=1.54 min.

EXAMPLE 46

5-Fluoro-1-methyl-N-(methylsulfonyl)-3-(4-(trifluoromethyl)phenyl)-1H-indole-6-carboxamide

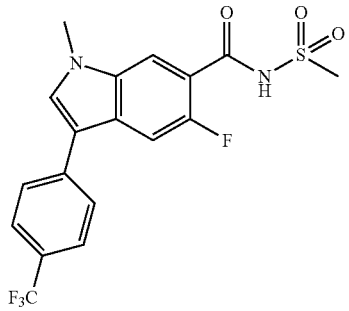 [SMILES: Cn1cc(-c2ccc(C(F)(F)F)cc2)c2cc(F)c(C(=O)NS(C)(=O)=O)cc21]

Prepared from intermediate R as described in Example 2, Part D. Obtained 8.0 mg, 55% yield. $^1$H NMR (500 MHz, DMSO-d6) δ 8.14 (s, 1H), 7.92 (dd, J=15.1, 7.2 Hz, 3H), 7.80-7.72 (m, 3H), 3.93 (s, 3H), 3.26 (s, 3H); $^{19}$F NMR (471 MHz, DMSO-d6) δ-60.64, -123.71; LCMS (ESI) m/e 413.1 [(M–H)$^+$, calcd C$_{18}$H$_{13}$F$_4$N$_2$O$_3$S$_1$, 413.1]; LC/MS retention time (method A): t$_R$=1.46 min.

EXAMPLE 47

N-(Cyclopropylsulfonyl)-5-fluoro-1-methyl-3-(4-(fluoromethyl)phenyl)-1H-indole-6-carboxamide

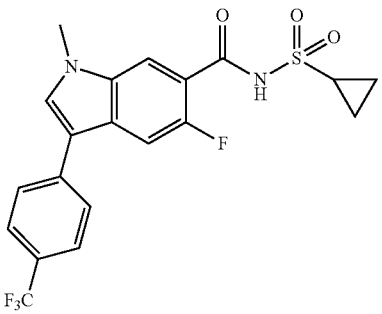 [SMILES: Cn1cc(-c2ccc(C(F)(F)F)cc2)c2cc(F)c(C(=O)NS(=O)(=O)C3CC3)cc21]

Prepared from intermediate R as described in Example 2, Part D. Obtained 6.3 mg, 44% yield. $^1$H NMR (500 MHz, DMSO-d6) δ 8.17 (s, 1H), 7.93 (dd, J=17.8, 7.0 Hz, 3H), 7.81-7.75 (m, 3H), 3.94 (s, 3H), 3.12 (ddd, J=12.9, 7.8, 4.8 Hz, 1H), 1.23-1.07 (m, 4H); $^{19}$F NMR (471 MHz, DMSO-d6) δ-60.66, -123.65; LCMS (ESI) m/e 439.1 [(M–H)$^+$, calcd C$_{20}$H$_{15}$F$_4$N$_2$O$_3$S$_1$, 439.1]; LC/MS retention time (method A): t$_R$=1.53 min.

EXAMPLE 48

3-(4-(Difluoromethyl)phenyl)-5-fluoro-1-methyl-N-(methylsulfonyl)-1H-indole-6-carboxamide

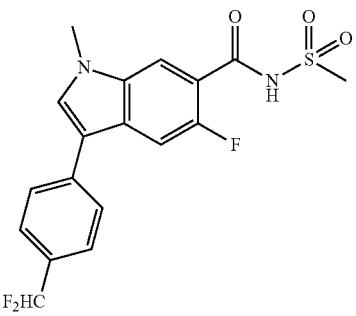 [SMILES: Cn1cc(-c2ccc(C(F)F)cc2)c2cc(F)c(C(=O)NS(C)(=O)=O)cc21]

Prepared from intermediate S as described in Example 2, Part D. Obtained 4.4 mg, 32% yield. $^1$H NMR (500 MHz, DMSO-d6) δ 8.12 (s, 1H), 7.96 (d, J=5.9 Hz, 1H), 7.83 (d, J=8.0 Hz, 2H), 7.77 (d, J=12.0 Hz, 1H), 7.64 (d, J=8.1 Hz, 2H), 7.07 (t, J=56.1 Hz, 1H), 3.94 (s, 3H), 3.38 (s, 3H); $^{19}$F NMR (471 MHz, DMSO-d6) δ-108.71, -124.14; LCMS (ESI) me 395.1 [(M–H)$^+$, calcd C$_{18}$H$_{14}$F$_3$N$_2$O$_3$S$_1$, 395.1]; LC/MS retention time (method A): t$_R$=1.37 min.

EXAMPLE 49

N-(Cyclopropylsulfonyl)-3-(4-(difluoromethyl)phenyl)-5-fluoro-1-methyl-1H-indole-6-carboxamide

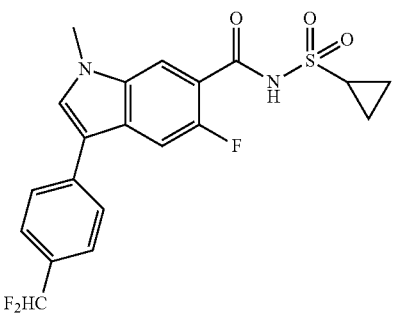 [SMILES: Cn1cc(-c2ccc(C(F)F)cc2)c2cc(F)c(C(=O)NS(=O)(=O)C3CC3)cc21]

Prepared from intermediate S as described in Example 2, Part D. Obtained 6.1 mg, 47% yield. $^1$H NMR (500 MHz, DMSO-d6) δ 8.12 (s, 1H), 7.94 (d, J=6.0 Hz, 1H), 7.83 (d, J=8.0 Hz, 2H), 7.77 (d, J=12.0 Hz, 1H), 7.64 (d, J=8.0 Hz, 2H), 7.07 (t, J=56.1 Hz, 1H), 3.94 (s, 3H), 3.14 (tt, J=7.9, 4.9 Hz, 1H), 1.23-1.10 (m, 4H); $^{19}$F NMR (471 MHz, DMSO-d6) δ-108.70, -123.94; LCMS (ESI) m/e 421.2 [(M-H)$^+$, calcd $C_{20}H_{16}F_3N_2O_3S_1$, 421.1]; LC/MS retention time (method A): $t_R$=1.44 min.

It will be evident to one skilled in the art that the present disclosure is not limited to the foregoing illustrative examples, and that it can be embodied in other specific forms without departing from the essential attributes thereof. The examples therefore should be considered in all respects as illustrative and not restrictive, reference being made to the appended claims, rather than to the foregoing examples, and all changes which come within the meaning and range of equivalency of the claims are therefore intended to be embraced.

We claim:

1. A compound of formula I

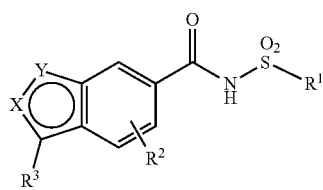

where:

X is CH and Y is NR$^4$;

or X is NR$^5$ and Y is N;

or X is N and Y is NR$^5$;

R$^1$ is alkyl, haloalkyl, cycloalkyl, NR$^6$R$^7$, or Ar$^1$;

R$^2$ is hydrogen or halo;

R$^3$ is phenyl, pyridinyl, pyridazinyl, pyrimidinyl, or pyrazinyl, and is substituted with 0-3 substituents selected from cyano, halo, alkyl, haloalkyl, alkoxy, (cycloalkyl)alkoxy, haloalkoxy, and NHCO$_2$R$^8$;

R$^4$ is hydrogen or alkyl;

R$^5$ is hydrogen or alkyl;

R$^6$ is hydrogen or alkyl;

R$^7$ is hydrogen or alkyl;

or NR$^6$R$^7$ taken together is azetidinyl, pyrrolidinyl, piperidinyl, piperazinyl, or morpholinyl, and is substituted with 0-3 halo or alkyl substituents;

R$^8$ is alkyl; and

Ar$^1$ is phenyl or thienyl and is substituted with 0-3 substituents selected from cyano, halo, alkyl, haloalkyl, alkoxy, and haloalkoxy;

or a pharmaceutically acceptable salt thereof.

2. A compound of claim 1 where X is CH and Y is NR$^4$.

3. A compound of claim 1 where X is NR$^5$ and Y is N.

4. A compound of claim 1 where X is N and Y is NR$^5$.

5. A compound of claim 1 where R$^3$ is phenyl substituted with 0-3 substituents selected from cyano, halo, alkyl, haloalkyl, alkoxy, (cycloalkyl)alkoxy, haloalkoxy, and NHCO$_2$R$^8$.

6. A compound of claim 1 where R$^3$ is pyridinyl, pyridazinyl, pyrimidinyl, or pyrazinyl, and is substituted with 0-3 substituents selected from cyano, halo, alkyl, haloalkyl, alkoxy, (cycloalkyl)alkoxy, haloalkoxy, and NHCO$_2$R$^8$.

7. A compound of claim 1 where Ar$^1$ is phenyl substituted with 0-3 substituents selected from cyano, halo, alkyl, haloalkyl, alkoxy, and haloalkoxy.

8. A pharmaceutical composition comprising a therapeutically effective amount of a compound of Formula I, or a pharmaceutically acceptable salt thereof, and a pharmaceutically acceptable carrier.

9. A method for treating pain in a patient in need thereof, comprising administering a therapeutically effective amount of a compound of Formula I, or a pharmaceutically acceptable salt thereof, with a pharmaceutically acceptable carrier to said patient.

* * * * *